(12) United States Patent
Ordentlich

(10) Patent No.: US 11,397,184 B2
(45) Date of Patent: Jul. 26, 2022

(54) SELECTION OF PATIENTS FOR COMBINATION THERAPY

(71) Applicant: Syndax Pharmaceuticals, Inc., Waltham, MA (US)

(72) Inventor: Peter Ordentlich, Lexington, MA (US)

(73) Assignee: SYNDAX PHARMACEUTICALS, INC., Waltham, MA (US)

(*) Notice: Subject to any disclaimer, the term of this patent is extended or adjusted under 35 U.S.C. 154(b) by 46 days.

(21) Appl. No.: 15/756,898

(22) PCT Filed: Sep. 2, 2016

(86) PCT No.: PCT/US2016/050274
§ 371 (c)(1),
(2) Date: Mar. 1, 2018

(87) PCT Pub. No.: WO2017/041043
PCT Pub. Date: Mar. 9, 2017

(65) Prior Publication Data
US 2018/0252721 A1 Sep. 6, 2018

Related U.S. Application Data

(60) Provisional application No. 62/219,612, filed on Sep. 16, 2015, provisional application No. 62/213,288, filed on Sep. 2, 2015.

(51) Int. Cl.
| | | |
|---|---|---|
| A61K 45/06 | (2006.01) | |
| A61P 35/00 | (2006.01) | |
| A61P 35/04 | (2006.01) | |
| G01N 33/574 | (2006.01) | |
| G01N 33/50 | (2006.01) | |
| G01N 33/569 | (2006.01) | |
| A61K 31/4406 | (2006.01) | |
| A61K 31/5685 | (2006.01) | |
| A61K 39/395 | (2006.01) | |
| C07K 16/28 | (2006.01) | |

(52) U.S. Cl.
CPC ... *G01N 33/57492* (2013.01); *A61K 31/4406* (2013.01); *A61K 31/5685* (2013.01); *A61K 39/3955* (2013.01); *A61K 45/06* (2013.01); *C07K 16/2827* (2013.01); *G01N 33/5091* (2013.01); *G01N 33/56972* (2013.01); *C07K 2317/24* (2013.01); *G01N 2800/52* (2013.01)

(58) Field of Classification Search
CPC ....... G01N 33/57492; G01N 33/56972; A61K 39/3955; A61K 45/06
USPC .................................................. 424/133.1
See application file for complete search history.

(56) References Cited

U.S. PATENT DOCUMENTS

| | | | |
|---|---|---|---|
| 8,500,712 B2 | 8/2013 | Polettini et al. | |
| 10,226,472 B2 * | 3/2019 | Goodenow | ........ A61K 31/5685 |
| 2012/0070461 A1 | 3/2012 | Singh et al. | |
| 2012/0276004 A1 | 11/2012 | Epstein et al. | |
| 2014/0378420 A1 | 12/2014 | Goodenow et al. | |

FOREIGN PATENT DOCUMENTS

| | | |
|---|---|---|
| WO | WO 2013/033656 A1 | 3/2013 |
| WO | WO 2014/011713 A2 | 1/2014 |
| WO | WO 2014/085461 A1 | 6/2014 |
| WO | WO 2016/010879 A1 | 1/2016 |
| WO | 2016/154068 A1 | 9/2016 |

OTHER PUBLICATIONS

Ang Huang et al. "Increased CD14+HLA-DR-/low myeloid-derived suppressor cells correlate with extrathoracic metastasis and poor response to chemotherapy in non-small cell lung cancer patients", Cancer Immunology, Immunotherapy, vol. 62, 2013, pp. 1439-1451.
Lin, Y. et al., Immunosuppressive CD14 Hladr Monocytes in B-Cell Non-Hodgkin Lymphoma Blood, Jan. 20, 2011; vol. 117, No. 3; pp. 1-19.
Thurn, KT et al., Rational Therapeutic Combinations with Histone Deacetylase Inhibitors for the Treatment of Cancer, Future Oncology. Feb. 2011; vol. 7, No. 2; pp. 1-34.
Kim, K. et al. "Eradication of metastatic mouse cancers resistant to immune checkpoint blockade by suppression of myeloid-derived cells", PNAS, 2014, vol. 111, No. 32, p. 11774-11779.
Vetsika, E. et al. "A Circulating Subpopulation of Monocytic Myeloid-Derived Suppressor Cells as an Independent Prognostic/Predictive Factor in Untreated Non-Small Lung Cancer Patients", Journal of Immunology Research, 2014, vol. 2014, Article ID 659294, 12 pages.
Rudolph et al., "Increased frequencies of CD11b+ CD33+CD14+ HLA-DRlow myeloid-derived suppressor cells are an early event in melanoma patients", Experimental Dermatology, 2014, vol. 23, pp. 199-218.
"Syndax and merck to collaborate on immuno-oncology study evaluating entinostat in combination with keytruda in lung cancer and melanoma", 2015, 5 pages. Retrieved online: https://www.europeanpharmaceuticalreview.com/news/30492/syndax-and-merck-to-collaborate-on-immunooncology-study-evaluating-entinostat-in-combinationwith-keytmda-in-lung-cancer-and-melanoma.

\* cited by examiner

*Primary Examiner* — Yan Xiao
(74) *Attorney, Agent, or Firm* — Cooley LLP; Heidi A. Erlacher; Eric A. Owens

(57) ABSTRACT

Described herein are methods for selecting cancer patients for treatment with a combination therapy comprising entinostat and a second therapeutic agent. In particular, methods are provided for the examination of a non-cancer cell type, myeloid-derived suppressor cells, e.g., those which are CD14-positive and HLA-DR-(lo/negative), as a therapeutic indicator in the setting of entinostat combination therapies.

19 Claims, 8 Drawing Sheets

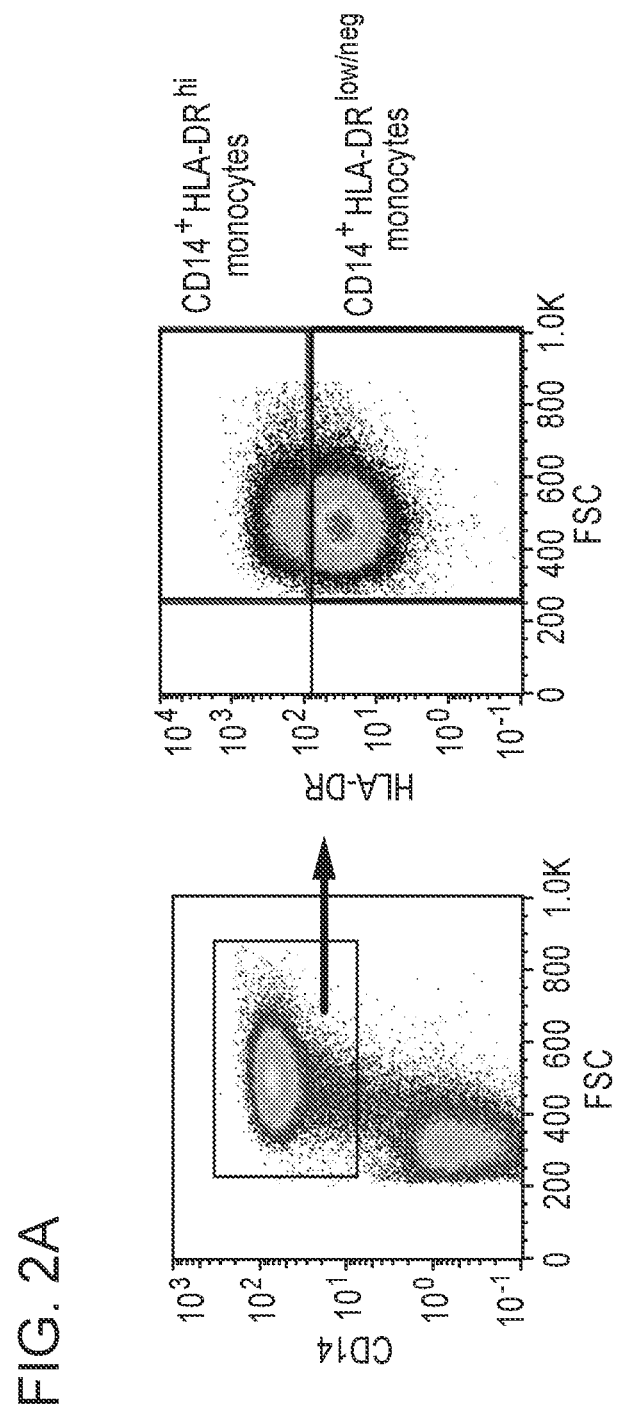

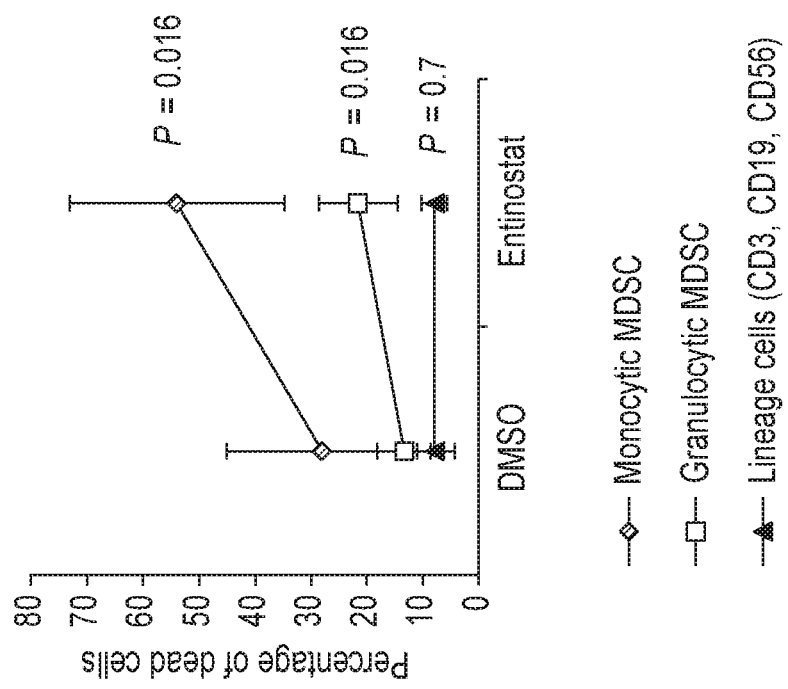
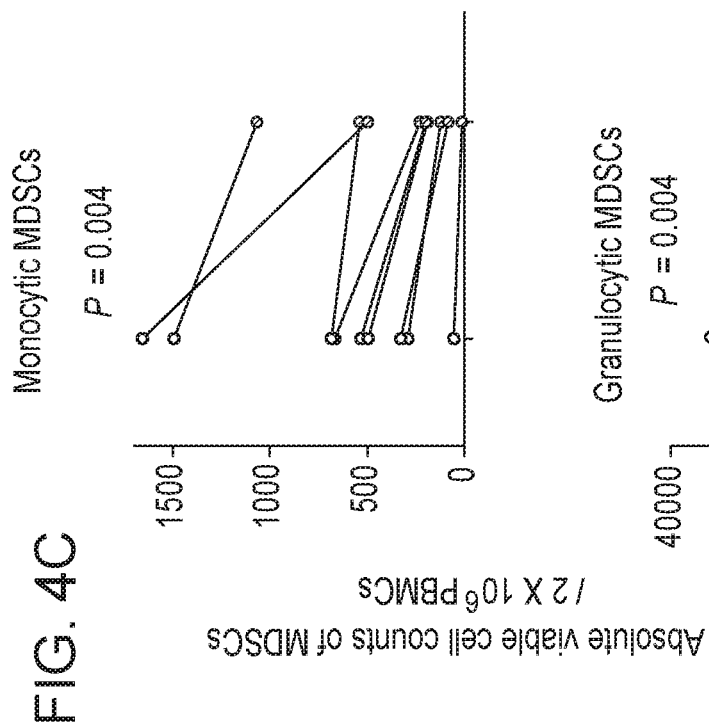
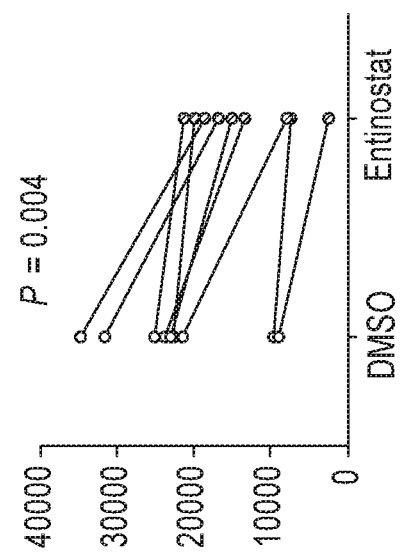

SELECTION OF PATIENTS FOR COMBINATION THERAPY

RELATED APPLICATIONS

This application is a national stage application of and claims priority to International Patent Application No. PCT/US2016/050274 filed Sep. 2, 2016, which in turn claims the benefit of U.S. Provisional Application Nos. 62/213,288, filed Sep. 2, 2015, and 62/219,612, filed Sep. 16, 2015, the contents of each of which are hereby incorporated by reference in their entireties.

BACKGROUND

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

HDAC inhibitors (HDACi) are an emerging class of therapeutic agents that promote differentiation and apoptosis in hematologic and solid malignancies through chromatin remodeling and gene expression regulation. Although the antitumor effects of HDACi have been studied, the impact of HDACi on cancer patient systemic immunity remains unclear.

There is a need for cancer immunotherapy in multiple indications, e.g., to increase the effectiveness of the antitumor agents and reduce and/or eliminate the side effects typically associated with conventional treatment.

SUMMARY

In one aspect, provided herein is a method of selecting a patient for combination therapy comprising entinostat and a second therapeutic agent. The method comprises obtaining a peripheral blood sample from the patient, wherein the patient is diagnosed with a cancer, measuring the number of myeloid derived suppressor cells and peripheral blood mononuclear cells in the peripheral blood sample; and administering the combination therapy if the ratio of myeloid derived suppressor cells to peripheral blood mononuclear cells is between 1:200 and 1:4.

In another aspect, provided herein is a method of selecting a patient for combination therapy comprising entinostat and a second therapeutic agent. The method comprises obtaining a peripheral blood sample from the patient, wherein the patient is diagnosed with a cancer, contacting one or more myeloid derived suppressor cells from the peripheral blood sample with a first binding agent to generate one or more first binding agent-myeloid derived suppressor cell complexes, contacting one or more peripheral blood mononuclear cells from the peripheral blood sample with a second binding agent to generate one or more second binding agent-peripheral blood mononuclear cell complexes, measuring a ratio of the first binding agent-myeloid derived suppressor cell complexes and the second binding agent-peripheral blood mononuclear cell complexes in the peripheral blood sample, and administering the combination therapy if the ratio of first binding agent-myeloid derived suppressor cell complexes to second binding agent-peripheral blood mononuclear cell complexes is between 1:200 and 1:4.

In another aspect, provided herein is a method of providing a prognosis for cancer in a patient comprising obtaining a peripheral blood sample from the patient, wherein the patient is diagnosed with a cancer, measuring the number of myeloid derived suppressor cells and peripheral blood mononuclear cells in the peripheral blood sample, wherein the method further comprises, administering a combination therapy comprising entinostat and a second therapeutic agent to the patient, if the ratio of myeloid derived suppressor cells to peripheral blood mononuclear cells is between 1:200 and 1:4.

In yet another aspect, provided herein is a method of selecting a patient for combination therapy comprising entinostat and a second therapeutic agent comprising: obtaining a peripheral blood sample from the patient, wherein the patient is diagnosed with a cancer; measuring the number of cells in the peripheral blood sample which are CD14-positive and HLA-DR-(lo/negative); measuring the number of cells in the peripheral blood sample which are CD-14 positive; and administering the combination therapy if the ratio of the CD14-positive and HLA-DR-(lo/negative) cells to CD-14 positive cells is between 1:100 and 99:1.

Provided in another aspect is a method of selecting a patient for combination therapy comprising entinostat and a second therapeutic agent comprising: obtaining a peripheral blood sample from the patient, wherein the patient is diagnosed with a cancer; measuring the number of cells in the peripheral blood sample which are CD14-positive and HLA-DR-(lo/negative); measuring the number peripheral blood mononuclear cells in the peripheral blood sample; and administering the combination therapy if the ratio of the CD14-positive and HLA-DR-(lo/negative) cells to peripheral blood mononuclear cells is between 1:200 and 1:1.

In still another aspect, provided herein is a method of providing a prognosis for cancer in a patient comprising: obtaining a peripheral blood sample from the patient, wherein the patient is diagnosed with a cancer; measuring the number of cells in the peripheral blood sample which are CD14-positive and HLA-DR-(lo/negative); measuring the number of cells in the peripheral blood sample which are CD-14 positive, wherein the method further comprises, administering a combination therapy comprising entinostat and a second therapeutic agent to the patient, if the ratio of CD14-positive and HLA-DR-(lo/negative) cells to CD-14 positive cells is between 1:100 and 99:1.

Also provided herein is a method of providing a prognosis for cancer in a patient comprising: obtaining a peripheral blood sample from the patient, wherein the patient is diagnosed with a cancer; measuring the number of cells in the peripheral blood sample which are CD14-positive and HLA-DR-(lo/negative); measuring the number of peripheral blood mononuclear cells in the peripheral blood sample, wherein the method further comprises, administering a combination therapy comprising entinostat and a second therapeutic agent to the patient, if the ratio of CD14-positive and HLA-DR-(lo/negative) cells to peripheral blood mononuclear cells is between 1:200 and 1:1.

FIG. 2 illustrates that entinostat increases HLA-DR expression on CD14$^+$ monocytes in breast cancer patients. (A) Gating strategy for analysis of CD14$^+$ monocytes (left panel), CD14$^+$HLA-DR$^{hi}$ monocytes (red box, right upper panel), and CD14$^+$HLA-DR$^{low/neg}$ monocytes (blue box, right lower panel) in PBMCs of breast cancer patients. Initially gated on single viable CD45$^+$ cells. (B) Change of % CD14$^+$HLA-DRhi monocytes among single viable CD45$^+$ PBMCs from baseline to C1D15 in exemestane plus placebo (EP) arm (n=14) and exemestane plus entinostat (EE) arm (n=20). The level of CD14$^+$HLA-DRhi monocytes was significantly increased in the EE arm compared to the EP arm (P=0.0004). (C) Change of HLA-DR expression (median fluorescence intensity, MFI) on CD14$^+$ monocytes from baseline to C1D15 in the EP arm (n=14) and EE arm (n=20). The level of HLA-DR expression on CD14$^+$ monocytes was significantly increased in the EE arm compared to the EP arm (P=0.015). (D) HLA-DR expression on CD14$^+$ monocytes in vitro. Fresh PBMCs were cultured with DMSO or entinostat (0.5 µM) for two days. Left panel shows a representative histogram of HLA-DR expression on CD14$^+$ monocytes cultured with DMSO (blue histogram) or with entinostat (red histogram). Black histogram shows isotype control. Right panel shows the difference of HLA-DR expression levels on CD14$^+$ monocytes cultured with DMSO or entinostat. Each line represents a different healthy donor (n=8, P=0.008). Median fluorescence intensity, MFI.

Figure 3A:
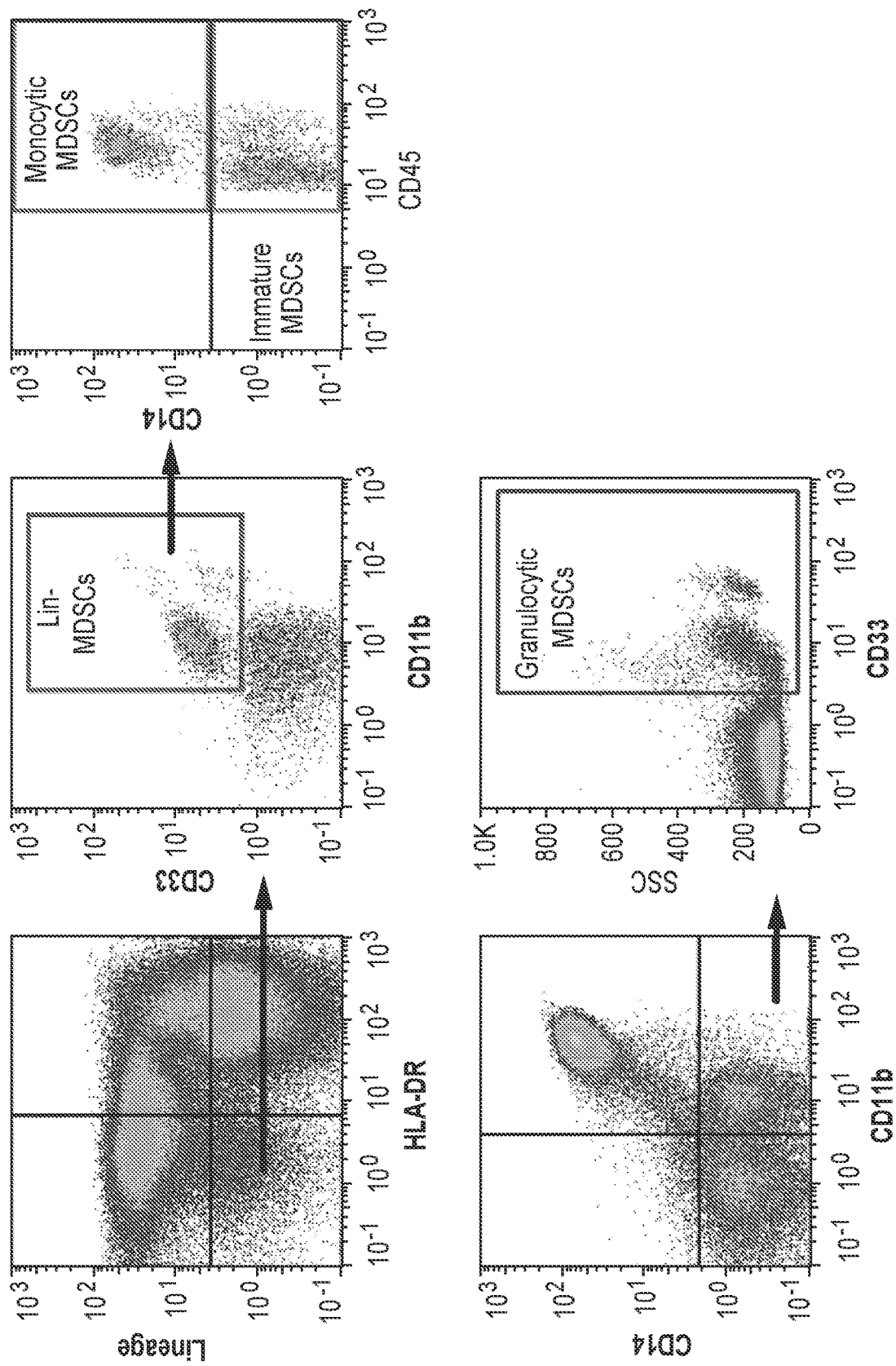
Figure 3B:
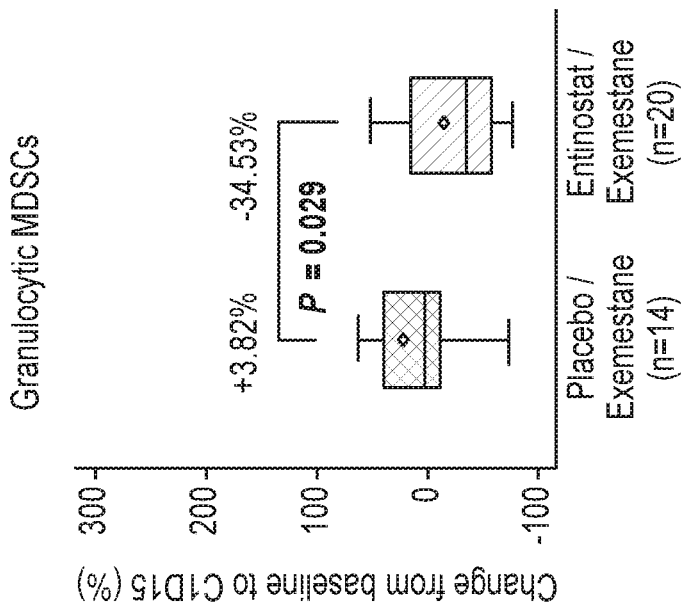
Figure 3C:
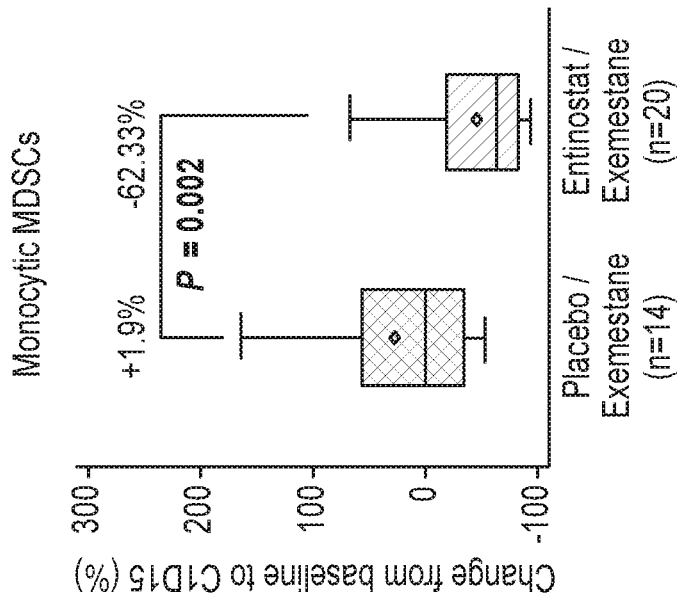

FIG. 3 illustrates that entinostat decreases monocytic MDSCs and granulocytic MDSCs in breast cancer patients. (A) Gating strategy for analysis of MDSC phenotypes in PBMCs of breast cancer patients. Initial gating was on single viable CD45$^+$ cells. Lineage (CD3, CD19, CD56)$^-$HLA-DR$^-$CD11b$^+$CD33$^+$ cells were defined as Lin$^-$MDSCs. The Lin$^-$MDSCs were further divided into monocytic MDSCs (Lin$^-$HLA-DR$^-$CD11b$^+$CD33$^+$CD14$^+$ cells) and immature MDSCs (Lin$^-$HLA-DR$^-$CD11b$^+$CD33$^+$CD14$^-$ cells). CD14$^-$CD11b$^+$CD33$^+$ cells were defined as granulocytic MDSCs. (B) Change of % monocytic MDSCs among single viable CD45$^+$ PBMCs from baseline to C1D15 in the exemestane plus placebo (EP) arm (n=14) and the exemestane plus entinostat (EE) arm (n=20). The level of monocytic MDSCs was significantly decreased in the EE arm compared to the EP arm (P=0.002). (C) Change of % granulocytic MDSCs among single viable CD45$^+$ PBMCs from baseline to C1D15 in the EP (n=14) and the EE arm (n=20). The level of granulocytic MDSCs was significantly decreased in the EE arm compared to the EP arm (P=0.029).

Figure 4B:
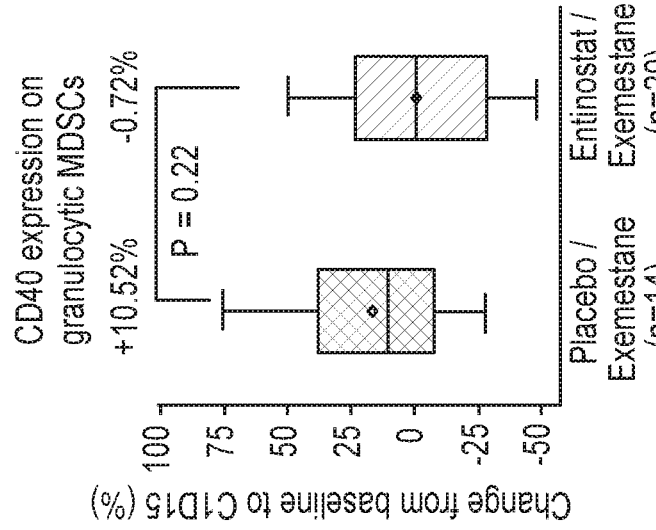
Figure 4A:
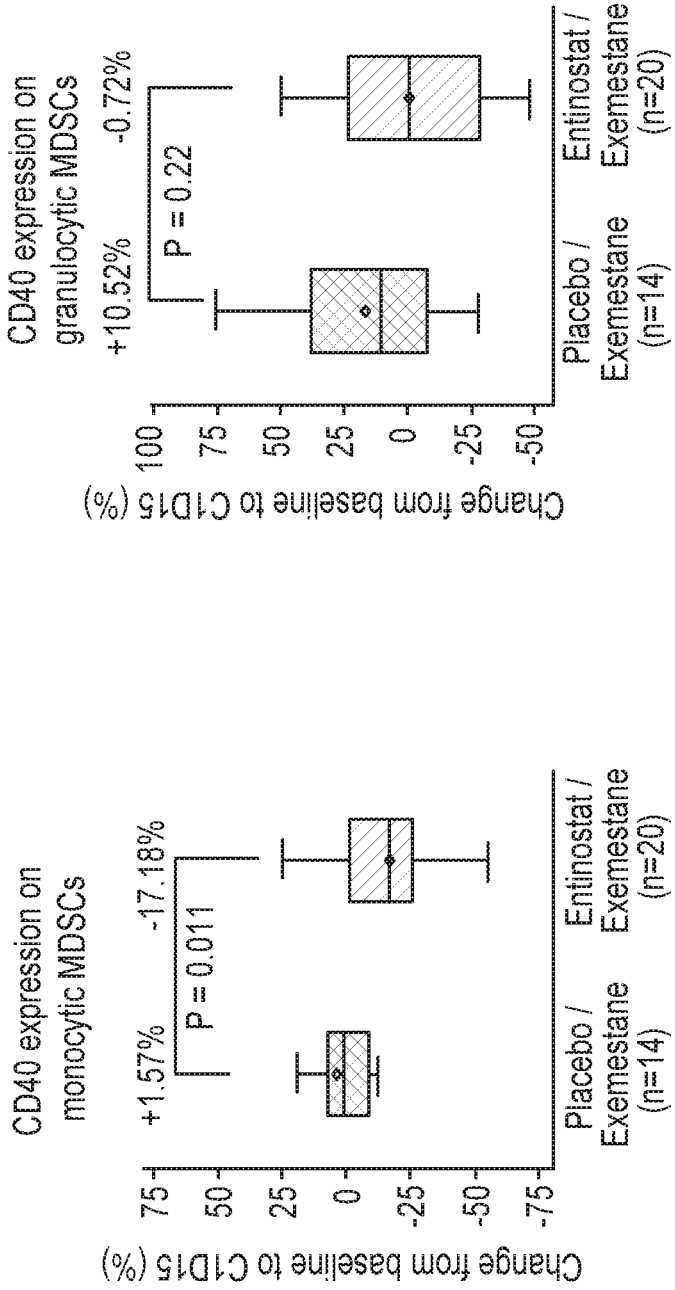

FIG. 4 illustrates that entinostat decreases CD40 expression on MDSCs in breast cancer patients. (A) Change of CD40 expression (MFI) on monocytic MDSCs from baseline to C1D15 in exemestane plus placebo (EP) arm (n=14) and exemestane plus entinostat (EE) arm (n=20). The level of CD40 on monocytic MDSCs was significantly decreased in the EE arm compared to the EP arm (P=0.011). (B) Change of CD40 expression (MFI) on granulocytic MDSCs from baseline to C1D15 in the EP arm (n=14) and the EE arm (n=20). The level of CD40 on granulocytic MDSCs did not show a statistically significant decrease in the EE arm compared to the EP arm (P=0.22). (C) Absolute viable cell counts of MDSCs (upper panel, monocytic MDSCs; lower panel, granulocytic MDSCs). Fresh PBMCs (2×10$^6$ PBMCs/well) were cultured with IL-6 (10 ng/ml) and GM-CSF (10 ng/ml). On day 5, DMSO or entinostat (0.5 µM) was added and cells were cultured for 3-4 days. Each line represents a different healthy donor (n=7; monocytic MDSCs, P=0.004; granulocytic MDSCs, P=0.004). (D) Percentage of dead cell dye-positive cells in the monocytic MDSCs (red line), granulocytic MDSCs (blue line), and Lineage cells (black line). Fresh PBMCs (2×10$^6$ PBMCs/well) were cultured with IL-6 and GM-CSF and then, DMSO or entinostat (0.5 µM) was added for two or three days and then cells were collected and stained with LIVE/DEAD Fixable Aqua Dead Cell Stain and antibodies. Percentage of dead cell dye-positive cells among each population (monocytic MDSCs, granulocytic MDSCs, and lineage cells) was calculated. Mean±SD is shown (n=7). Percentage of dead monocytic MDSCs and dead granulocytic MDSCs was increased by entinostat although the percentage of dead lineage cells was not increased. Monocytic MDSCs, P=0.016; Granulocytic MDSCs, P=0.016; Lineage cells (CD3$^+$, CD19$^+$, or CD56$^+$), P=0.7.

Figure 5A:
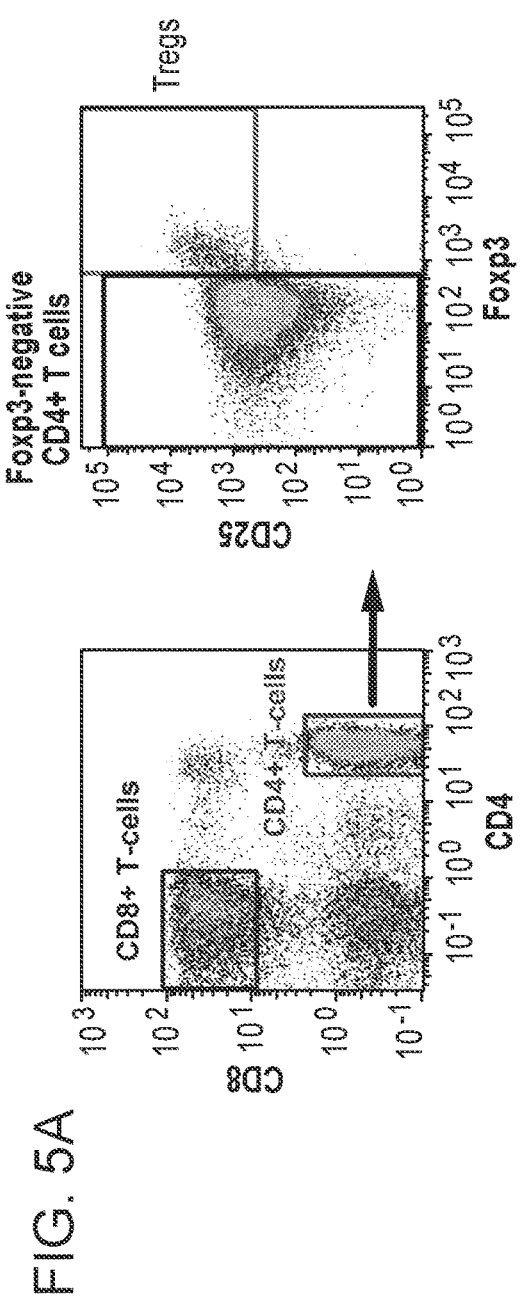
Figure 5B:
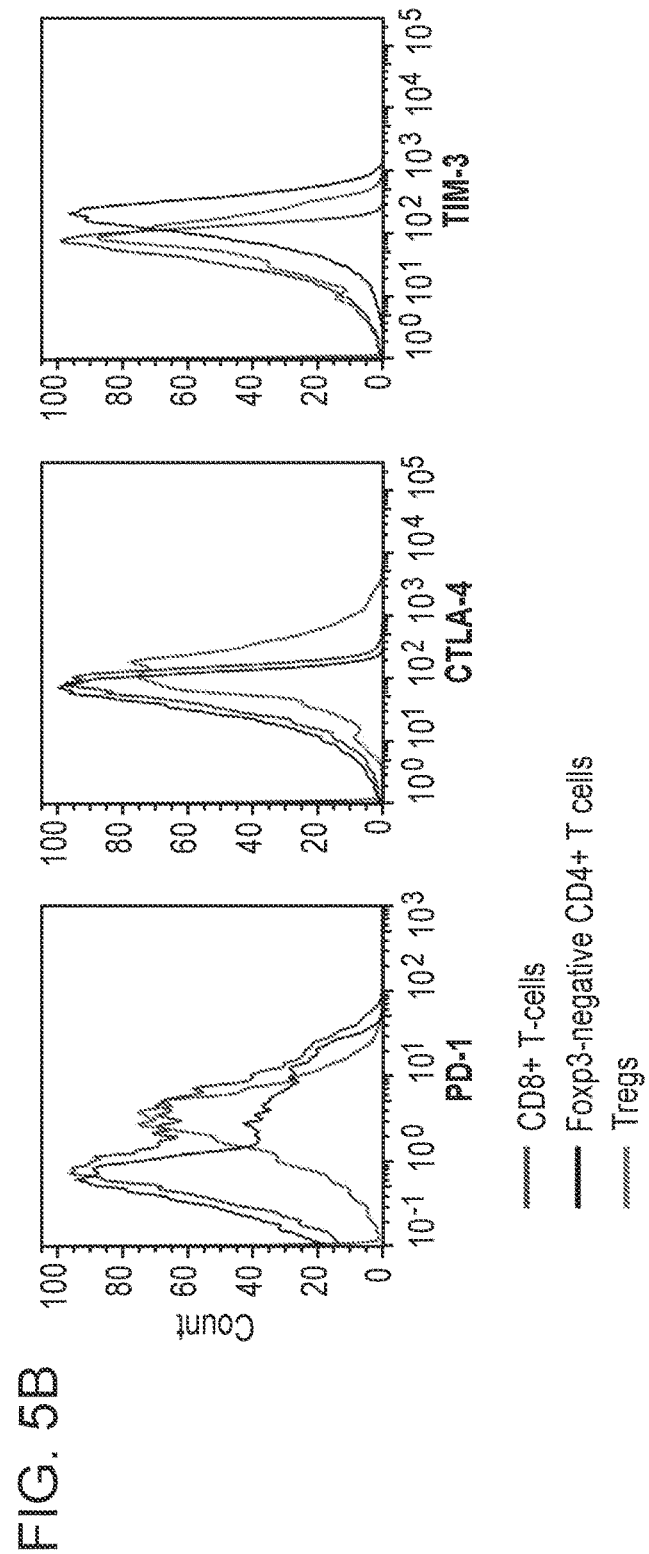

FIG. 5 illustrates gating strategy for analysis of T-cell subsets in PBMCs of breast cancer patients. (A) Initial gating was on single viable cells. The CD4$^+$ T-cells were further divided into Tregs (CD8$^-$CD4$^+$CD25$^{hi}$Foxp3$^+$ cells) and Foxp3$^-$CD4$^+$ T-cells (CD8$^-$CD4$^+$Foxp3$^-$ cells). (B) Immune checkpoint receptor expression was evaluated for CD8$^+$ T-cells, Foxp3$^-$CD4$^+$ T-cells, and Tregs. Representative histograms for PD-1 (left), CTLA-4 (middle), and TIM-3 (right) were shown.

DETAILED DESCRIPTION

Conventional approaches for selecting cancer patients for combination therapy rely upon assessment of the cancer, either in terms of histology or molecular analyses. The present disclosure provides methods that rely upon the levels of non-tumor myeloid derived suppressor cells, e.g., those which are CD14-positive and HLA-DR-(lo/negative), in a biological sample obtained from a cancer patient, as predictive and prognostic biomarker for selecting a patient for a combination therapy with entinostat and a second therapeutic agent.

In one aspect, the disclosure relates to a method of selecting a patient for combination therapy comprising entinostat and a second therapeutic agent, based on the ratio of myeloid derived suppressor cells and peripheral blood mononuclear cells, measured in peripheral blood sample collected from the patients, wherein the combination therapy is administered if the ratio of myeloid derived suppressor cells to peripheral blood mononuclear cells is between 1:200 and 1:4. Provided herein in another aspect is a method of selecting a patient for combination therapy comprising entinostat and a second therapeutic agent, based on the ratio of myeloid derived suppressor cells-first binding agent complexes and peripheral blood mononuclear cells-second binding agent complexes, measured in peripheral blood sample collected from the patients, wherein the complexes are formed by contacting the myeloid derived suppressor cells and the peripheral blood mononuclear cells with the first and second bindings respectively, and wherein the combination therapy is administered if the ratio of myeloid derived suppressor cell first binding agent complexes to peripheral blood mononuclear cell-second binding agent complexes is between 1:200 and 1:4. Further provided in another aspect is a method for providing a diagnosis and/or prognosis of cancer in a patient based on the ratio of myeloid derived suppressor cells and peripheral blood mononuclear cells, measured in peripheral blood sample collected from the patients, wherein the method further comprises administering a combination therapy comprising entinostat and a second therapeutic agent if the ratio of myeloid derived suppressor cells to peripheral blood mononuclear cells is between 1:200 and 1:4.

In yet another aspect, provided herein is a method of selecting a patient for combination therapy comprising entinostat and a second therapeutic agent comprising: obtaining a peripheral blood sample from the patient, wherein the patient is diagnosed with a cancer; measuring the number of cells in the peripheral blood sample which are CD14-positive and HLA-DR-(lo/negative); measuring the number of cells in the peripheral blood sample which are CD-14 positive; and administering the combination therapy if the ratio of the CD14-positive and HLA-DR-(lo/negative) cells to CD-14 positive cells is between 1:100 and 99:1. Provided in another aspect is a method of selecting a patient for combination therapy comprising entinostat and a second therapeutic agent comprising: obtaining a peripheral blood sample from the patient, wherein the patient is diagnosed with a cancer; measuring the number of cells in the peripheral blood sample which are CD14-positive and HLA-DR-(lo/negative); measuring the number peripheral blood mononuclear cells in the peripheral blood sample; and administering the combination therapy if the ratio of the CD14-positive and HLA-DR-(lo/negative) cells to peripheral blood mononuclear cells is between 1:200 and 1:1. Provided herein in yet another aspect is a method of providing a prognosis for cancer in a patient comprising: obtaining a peripheral blood sample from the patient, wherein the patient is diagnosed with a cancer; measuring the number of cells in the peripheral blood sample which are CD14-positive and HLA-DR-(lo/negative); measuring the number of cells in the peripheral blood sample which are CD-14 positive, wherein the method further comprises, administering a combination therapy comprising entinostat and a second therapeutic agent to the patient, if the ratio of CD14-positive and HLA-DR-(lo/negative) cells to CD-14 positive cells is between 1:100 and 99:1. Provided herein in another aspect, is a method of providing a prognosis for cancer in a patient comprising: obtaining a peripheral blood sample from the patient, wherein the patient is diagnosed with a cancer; measuring the number of cells in the peripheral blood sample which are CD14-positive and HLA-DR-(lo/negative); measuring the number of peripheral blood mononuclear cells in the peripheral blood sample, wherein the method further comprises, administering a combination therapy comprising entinostat and a second therapeutic agent to the patient, if the ratio of CD14-positive and HLA-DR-(lo/negative) cells to peripheral blood mononuclear cells is between 1:200 and 1:1.

In some embodiments, the peripheral blood sample is treated with an anticoagulant. In some embodiments, the anticoagulant is EDTA or heparin. In some embodiments, measuring number of cells in the peripheral blood sample which are CD14-positive and HLA-DR-(lo/negative) is performed by flow cytometry. In some embodiments, the peripheral blood mononuclear cell population is identified by a cell surface marker. In some embodiments, the cell surface marker is at least one of CD3, CD14, CD19, CD56, and HLA-DR. In some embodiments, the ratio of the CD14-positive and HLA-DR-(lo/negative) cells to CD-14 positive cells is between 1:50 and 99:1. In some embodiments, the ratio the ratio of the CD14-positive and HLA-DR-(lo/negative) cells to CD-14 positive cells is between 1:20 and 99:1. In some embodiments, the ratio of the CD14-positive and HLA-DR-(lo/negative) cells to CD-14 positive cells is between 1:10 and 99:1. In some embodiments, the ratio of the CD14-positive and HLA-DR-(lo/negative) cells to peripheral blood mononuclear cells is between 1:5 and 99:1. In some embodiments, the ratio of the CD14-positive and HLA-DR-(lo/negative) cells to peripheral blood mononuclear cells is between 1:50 and 1:4. In some embodiments, the ratio the ratio of the CD14-positive and HLA-DR-(lo/negative) cells to peripheral blood mononuclear cells is between 1:20 and 1:4. In some embodiments, the ratio of the CD14-positive and HLA-DR-(lo/negative) cells to peripheral blood mononuclear cells is between 1:10 and 1:4. In some embodiments, the ratio of the CD14-positive and HLA-DR-(lo/negative) cells to peripheral blood mononuclear cells is between 1:5 and 1:4.

In some embodiments, the entinostat is administered orally. In some embodiments, the entinostat is administered first. In some embodiments, the entinostat is administered weekly. In some embodiments, the entinostat is administered every two weeks. In some embodiments, the entinostat is administered at a dose of 5 mg. In some embodiments, the entinostat is administered at a dose of 5 mg weekly. In some embodiments, the entinostat is administered at a dose of 5 mg every two weeks.

In some embodiments, the second therapeutic agent is an anti-PD-1 antibody. In some embodiments, the anti-PD-1 antibody is pembrolizumab. In some embodiments, the anti-PD-1 antibody is nivolumab. In some embodiments, the cancer is a lung cancer. In some embodiments, the lung cancer is a non-small cell lung cancer, squamous cell carcinoma, or large cell carcinoma. In some embodiments, the cancer is a melanoma. In some embodiments, the melanoma is a metastatic melanoma. In some embodiments, the second therapeutic agent is an anti-PD-L1 antibody. In some embodiments, the anti-PD-L1 antibody is MPDL3280A. In some embodiments, the second therapeutic agent is exemestane. In some embodiments, the cancer is a breast cancer. In some embodiments, the second therapeutic agent is MPDL3280A and the breast cancer is a triple-negative breast cancer. In some embodiments, the second therapeutic agent is exemestane and the breast cancer is hormone receptor positive breast cancer. In some embodiments, the anti-PD-1 antibody or anti-PD-L1 antibody is administered by infusion. In some embodiments, the exemestane is administered orally.

To facilitate understanding of the disclosure set forth herein, a number of terms are defined below.

As used herein, "abnormal cell growth," refers to cell growth that is independent of normal regulatory mechanisms (e.g., loss of contact inhibition), including the abnormal growth of normal cells and the growth of abnormal cells.

"Neoplasia" as described herein, is an abnormal, unregulated and disorganized proliferation of cells that is distinguished from normal cells by autonomous growth and somatic mutations. As neoplastic cells grow and divide they pass on their genetic mutations and proliferative characteristics to progeny cells. A neoplasm, or tumor, is an accumulation of neoplastic cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma. Angiogenesis has been associated with blood-born tumors such as leukemias. It is believed that angiogenesis plays a role in the abnormalities in the bone marrow that give rise to leukemia. Prevention of angiogenesis could halt the growth of cancerous tumors and the resultant damage to the subject due to the presence of the tumor.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "lo/negative", when used to describe expression of a cell surface marker on a cell, corresponds to a low to absent level of expression of the cell surface marker on the cell relative to an unstained control cell. A low to absent level of expression can be about a 1-fold increase, about a 2-fold increase, about a 3-fold increase, about a 4-fold increase, about a 5-fold increase, about a 6-fold increase, about a 7-fold increase, about a 8-fold increase, about a 9-fold increase, about a 10-fold increase, can be about a 11-fold increase, about a 12-fold increase, about a 13-fold increase, about a 14-fold increase, about a 15-fold increase, about a 16-fold increase, about a 17-fold increase, about a 18-fold increase, about a 19-fold increase, or about a 20-fold increase relative to an unstained control cell. A low to absent level of expression can be from about a 1-fold increase to about a 2-fold increase, from about a 2-fold increase to about a 3-fold increase, from about a 3-fold increase to about a 4-fold increase, from about a 4-fold increase to about a 5-fold increase, from about a 5-fold increase to about a 6-fold increase, from about a 6-fold increase to about a 7-fold increase, from about a 7-fold increase to about a 8-fold increase, from about a 8-fold increase to about a 9-fold increase, from about a 9-fold increase to about a 10-fold increase, from about a 10-fold increase to about a 11-fold increase, from about a 11-fold increase to about a 12-fold increase, from about a 12-fold increase to about a 13-fold increase, from about a 13-fold increase to about a 14-fold increase, from about a 14-fold increase to about a 15-fold increase, from about a 15-fold increase to about a 16-fold increase, from about a 16-fold increase to about a 17-fold increase, from about a 17-fold increase to about a 18-fold increase, from about a 18-fold increase to about a 19-fold increase, or from about a 19-fold increase to about a 20-fold increase.

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

HDAC inhibitors are an emerging class of therapeutic agents that promote differentiation and apoptosis in hematologic and solid malignancies through chromatin remodeling and gene expression regulation. Several HDAC inhibitors have been identified including benzamides (entinostat), short-chain fatty acids (i.e., Sodium phenylbutyrate); hydroxamic acids (i.e., suberoylanilide hydroxamic acid and thrichostatin A); cyclic tetrapeptides containing a 2-amino-8-oxo-9,10-epoxy-decanoyl moiety (i.e., trapoxin A) and cyclic peptides without the 2-amino-8-oxo-9,10-epoxy-decanoyl moiety (i.e., FK228). Entinostat is a benzamide HDAC inhibitor undergoing clinical investigation in multiple types of solid tumors and hematologic cancers. Entinostat is rapidly absorbed and has a half-life of about 100 hours and, importantly, changes in histone acetylation persist for several weeks following the administration of entinostat.

Without being bound by any theory, it is contemplated that myeloid derived suppressor cells block effector anti-tumor T-cell activity and facilitate immune evasion. Myeloid derived suppressor cells are increased in breast cancer patients, with the highest levels of circulating myeloid derived suppressor cells being present in patients with metastatic disease. In the setting of metastatic breast cancer, patients with higher than average levels of peripheral blood myeloid derived suppressor cells following palliative systemic therapy had shorter overall survival. In the setting of adjuvant chemotherapy in breast cancer, reduced levels of circulating myeloid derived suppressor cells has been shown to be correlated with increased clinical efficacy. Functional studies in mouse models of breast cancer have found that depletion or inactivation of myeloid derived suppressor cells reduces tumor growth and progression through development of an anti-tumor immune response.

Without being bound by any theory, it is contemplated that depleting myeloid derived suppressor cells can act as a treatment for cancer through generation of an immune response against the tumor.

Myeloid-Derived Suppressor Cells

Myeloid derived suppressor cells are a heterogeneous population of immature myeloid cells which inhibit innate and adaptive immunity. Myeloid derived suppressor cells can inhibit innate and adaptive immunity through mechanisms including depletion of arginine, production of reactive nitrogen and oxygen species, and secretion of inhibitory cytokines.

Myeloid derived suppressor cells commonly express the cell surface markers CD33 and CD11b and have reduced expression of HLA-DR (HLA-DR lo/negative). Non-limiting examples of myeloid derived suppressor cells include monocytic myeloid derived suppressor cells (M-MDSCs) and polymorphonuclear myeloid derived suppressor cells (PMN-MDSCs). M-MDSCs express the cell surface marker CD14, are HLA-DR lo/negative, and do not express the cell surface marker CD15 in humans. PMN-MDSCs do not express the cell surface marker CD14 and express the cell surface marker CD15 in humans.

Myeloid derived suppressor cells cause inhibition of immune activator cells such as T lymphocytes, natural killer (NK) cells, and dendritic cells (DCs). Conversely, myeloid derived suppressor cells can be stimulatory to immune suppressor cells such as $T_h2$ T lymphocytes, T regulatory cells ($T_{res}$) and tumor-associated macrophages (TAMs). Myeloid derived suppressor cells can also secrete cytokines, such as IL-6, that promote MDSC expansion. The expansion of myeloid derived suppressor cells can lead to sequestration of essential amino acids such as arginine and cysteine necessary for the survival of T lymphocytes. Myeloid derived suppressor cells inhibit immunity through the production of reactive oxygen species, such as nitric oxide, which are potently toxic to T lymphocytes.

Histone Deacetylases

The HDACs are a family including at least eighteen enzymes, grouped in three classes (Class I, II and III). Class I HDACs include, but are not limited to, HDACs 1, 2, 3, and 8. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7. As used herein, the term "selective HDAC" refers to an HDAC inhibitor that does not interact with all three HDAC classes.

HDAC Inhibitors

HDAC inhibitors can be classified broadly into pan HDAC inhibitors and selective HDAC inhibitors. Although there is a large structural diversity of known HDAC inhibitors, they share common features: a part that interacts with the enzyme active site and a side-chain that sits inside the channel leading to the active site. This can be seen with the hydroxamates such as SAHA, where the hydroxamate group is believed to interact with the active site. In the case of the depsipeptides, it is believed that an intracellular reduction of the disulphide bond creates a free thiol group (which interacts with the active site) attached to a 4-carbon alkenyl chain. A difference between the HDAC inhibitors is in the way that they interact with the rim of the HDAC channel, which is at the opposite end of the channel to the active site. It is this interaction, between the HDAC inhibitor and the rim of the channel, which is believed to account, at least in part, for some observed differences in HDAC selectivity between pan-HDAC inhibitors, such as SAHA and selective HDAC inhibitors such as the depsipeptides. A particularly preferred HDAC inhibitor is entinostat. Entinostat has the chemical name N-(2-aminophenyl)-4-[N-(pyridine-3-yl) methoxycarbonylamino-methyl]-benzamide and the chemical structure shown below.

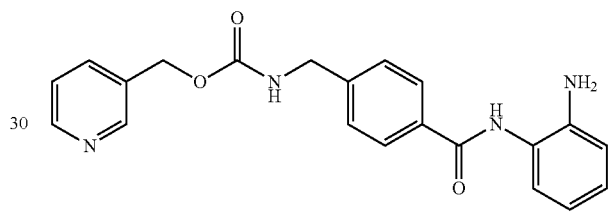

Chemical structure of entinostat

Programmed Cell Death-1 (PD-1)

PD-1 is a cell surface receptor that is a member of the CD28 family of T-cell regulators, within the immunoglobulin superfamily of receptors. The human PD-1 gene is located at chromosome 2q37, and the full-length PD-1 cDNA encodes a protein with 288 amino acid residues with 60% homology to murine PD-1. It is present on CD4− CD8− (double negative) thymocytes during thymic development and is expressed upon activation in mature hematopoietic cells such as T and B cells, NKT cells and monocytes after prolonged antigen exposure.

Without being bound by any theory, it is contemplated that binding of the ligand PD-L1 to PD-1 downregulates effector anti-tumor T-cell activity and facilitates immune evasion. This is supported by the finding of an association between PD-1/PD-L1 expression and poor prognosis in several tumor types including gastric, ovarian, lung and renal carcinomas. PD-1 has been reported to be predominantly expressed by tumor infiltrating T lymphocytes, in melanoma.

In vitro studies of PD-1 blockade by PD-1-specific antibody showed augmentation of cytotoxic T-cell responses to melanoma-specific antigens including increased frequencies of IFN-γ-secreting antigen-specific cells.

Without being bound by any theory, it is contemplated that targeting PD-1 may act as an effective therapeutic strategy for cancer.

The principal method for targeting PD-1 clinically has been through the development of genetically engineered monoclonal antibodies that inhibit either PD-1 or PD-L1 function.

PD-L1 has also been shown to bind to B7-1 (CD80), an interaction that also suppresses T-cell proliferation and cytokine production; however, the exact relative contributions of the PD-L1: PD-1 and PD-L1: B7-1 pathways in cancer remain unclear. The PD-1-targeting agents currently in development inhibit both pathways. However, as the binding sites for PD-1 and B7-1 are adjacent but not overlapping, agents that specifically target one or the other may potentially be developed.

Cancer cells drive high expression levels of PD-L1 on their surface, allowing activation of the inhibitory PD-1 receptor on any T cells that infiltrate the tumor microenvironment, effectively switching those cells off. Indeed, upregulation of PD-L1 expression levels has been demonstrated in many different cancer types (eg, melanoma [40%-100%], NSCLC [35%-95%], and multiple myeloma [93%]), and high levels of PD-L1 expression have been linked to poor clinical outcomes. Furthermore, tumor-infiltrating T cells have been shown to express significantly higher levels of PD-1 than T cells that infiltrate normal tissue. It is thought that the tumor microenvironment may secrete pro-inflammatory cytokines, including interferon-gamma (IFNγ) to upregulate the expression of PD-1 on tumor-infiltrating T cells to ensure that they can respond to the high levels of PD-L1 expressed on the tumor.

Pembrolizumab

Pembrolizumab is a humanized monoclonal IgG4 anti-PD-1 antibody consisting of a high-affinity mouse anti-PD-1-derived variable region grafted on to a human IgG4 immunoglobulin molecule with an engineered Fc region for stabilization. Pre-clinical anti-tumor activity has been demonstrated in animal models of multiple tumor types. A first-in-human, Phase I dose-escalation study was conducted in patients with advanced refractory malignancies at dose levels 1, 3 and 10 mg/kg given intravenously initially and after 4 weeks and then every 2 weeks. The maximum observed toxicity was grade 2 pruritus and no drug-related grade 3 or greater adverse events (AEs) were observed. Therefore, the maximum tolerated dose was not reached. The half-life was 13.6-21.7 days and not obviously dose related. Four patients had some tumor regression. This study was then expanded, with patients receiving pembrolizumab at 10 mg/kg every 2 weeks or either 2 or 10 mg/kg every 3 weeks in non-randomized cohorts; in total, there were 135 patients with melanoma. Enrollment included 48 patients who had received prior ipilimumab but could not have experienced severe immune-related adverse events (irAEs). Though 79% of patients had some AEs, only 13% had severe (grade 3 or 4) drug-related toxicities including skin rash or pruritus, fatigue, diarrhea, abdominal pain and hepatic dysfunction. The highest rate of severe toxicities (23%) was in those receiving the highest dose (10 mg/kg every 2 weeks) versus <10% in the less dose intense cohorts. AEs potentially of an autoimmune nature included isolated instances of pneumonitis, kidney injury, hepatitis, diarrhea, hypothyroidism, hyperthyroidism and adrenal insufficiency. The overall objective response rate (ORR) based on immune-related response criteria was 38% (44 of 117) with 8 additional patients experiencing unconfirmed responses. A total of 77% had some degree of tumor regression including 8 patients with stable disease for over 24 weeks. The majority of responses were established by the time of the first radiologic assessment at 12 weeks. The median progression free survival exceeded 7 months. Biopsies of responding tumors showed dense infiltration by CD8$^+$ T cells. Prior ipilimumab exposure did not appear to have an obvious impact on efficacy or toxicity outcomes.

MPDL3280A

MPDL3280A is a human anti-PD-L1 mAb that contains an engineered fragment crystallizable (Fc) domain designed to optimize efficacy and safety by minimizing antibody-dependent cellular cytotoxicity (ADCC). Without being bound by any specific theory, it is understood that this structure allows inhibition of the PD-1/PD-L1 interaction, while minimizing ADCC-mediated depletion of activated T cells that is required for an effective antitumor immune response.

MPDL3280A has been evaluated in a phase I trial in patients with locally advanced or metastatic solid tumors. A total of 175 patients had been recruited to date. The antibody was administered as a single agent at escalating doses of ≤1, 3, 10, 15, and 20 mg/kg for a median duration of 127 days. The results of two expansion cohorts have also been reported; a cohort of 85 patients (53 of whom were evaluable for efficacy) with squamous or non-squamous NSCLC and a cohort of 45 metastatic melanoma patients (35 of whom were evaluable for efficacy). In both cohorts doses of ≤1, 10, 15, and 25 mg/kg MPDL3280A were administered every 3 weeks for up to 1 year. MPDL3280A demonstrated durable responses and was well tolerated; efficacy data are summarized in Table 1. Of the 85 patients in the NSCLC cohort, 55% were heavily pretreated with at least three prior therapies, and 81% were smokers or ex-smokers and 19% were never-smokers. The 24-week PFS rate was 44% in squamous cell NSCLC and 46% in non-squamous cell NSCLC.

Exemestane

Exemestane is a drug used to treat breast cancer. It is a member of the class of drugs known as aromatase inhibitors. Some breast cancers require hormones to grow. Those cancers, known as hormone receptor-positive breast cancers, express either estrogen receptors (ERs) or progesterone receptors (PRs), and thus termed as ER-positive or PR-positive breast cancers. The main source of estrogen in pre-menopausal women is the ovaries, while in post-menopausal women most of the body's estrogen is produced via the conversion of androgens into estrogen by the aromatase enzyme in peripheral tissues, such as in adipose mammary tissue and the brain. Exemestane is an aromatase inhibitor used in ER-positive breast cancer in addition to surgery or radiation in post-menopausal women. Exemestane is an irreversible, oral steroidal aromatase inactivator, structurally related to the natural substrate androstenedione. It acts as a false substrate for the aromatase enzyme, and is processed to an intermediate that binds irreversibly to the aromatase active site to block aromatase by suicide inhibition.

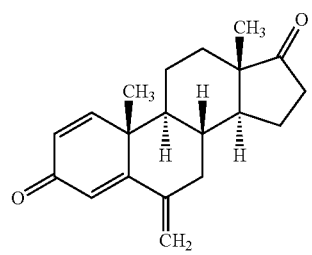

Chemical structure of exemestane

Exemestane is indicated for the adjuvant treatment of post-menopausal women with ER-positive early breast cancer who have received two to three years of tamoxifen. Subjects are switched to it for completion of a total of five consecutive years of adjuvant hormonal therapy. Exemestane is also indicated for the treatment of advanced breast cancer in postmenopausal women whose disease has progressed following tamoxifen therapy. Oral exemestane at 25 mg per day for two to three years of adjuvant therapy was generally more effective than five years of continuous adjuvant tamoxifen in the treatment of post-menopausal women with early-stage ER-positive or unknown receptor status breast cancer. Exemestane at 25 mg per day is also effective in the primary adjuvant setting of early-stage breast cancer in post-menopausal women.

Lung Cancer

Lung cancer is the leading cause of cancer deaths in women and men both in the United States and throughout the world. Lung cancer has surpassed breast cancer as the leading cause of cancer deaths in women. In the United States in 2014, 158,040 people were projected to die from lung cancer, which is more than the number of deaths from colon and rectal, breast, and prostate cancer combined. Only about 2% of those diagnosed with lung cancer that has spread to other areas of the body are alive five years after the diagnosis, although the survival rates for lung cancers diagnosed at the earliest stage are higher, with approximately 49% surviving for five years or longer.

Cancer occurs when normal cells undergo a transformation that causes them to grow and multiply without control. The cells form a mass or tumor that differs from the surrounding tissues from which it arises. Tumors are dangerous because they take oxygen, nutrients, and space from healthy cells and because they invade and destroy or reduce the ability of normal tissues to function.

Most lung tumors are malignant. This means that they invade and destroy the healthy tissues around them and can spread throughout the body. The tumors can spread to nearby lymph nodes or through the bloodstream to other organs. This process is called metastasis. When lung cancer metastasizes, the tumor in the lung is called the primary tumor, and the tumors in other parts of the body are called secondary tumors or metastatic tumors.

Some tumors in the lung are metastatic from cancers elsewhere in the body. The lungs are a common site for metastasis. If this is the case, the cancer is not considered to be lung cancer. For example, if prostate cancer spreads via the bloodstream to the lungs, it is metastatic prostate cancer (a secondary cancer) in the lung and is not called lung cancer.

Lung cancer comprises a group of different types of tumors. Lung cancers usually are divided into two main groups that account for about 95% of all cases. The division into groups is based on the type of cells that make up the cancer. The two main types of lung cancer are characterized by the cell size of the tumor when viewed under the microscope. They are called small cell lung cancer (SCLC) and non-small cell lung cancer (NSCLC). NSCLC includes several subtypes of tumors. SCLCs are less common, but they grow more quickly and are more likely to metastasize than NSCLCs. Often, SCLCs have already spread to other parts of the body when the cancer is diagnosed. About 5% of lung cancers are of rare cell types, including carcinoid tumor, lymphoma, and others. As used herein, the term "lung cancer" includes, but is not limited to, SCLC, NSCLC, carcinoid tumor, lymphoma, and their various subtypes.

Myeloid derived suppressor cells have several important functions in lung cancer. Pre-clinically, mouse models demonstrate that myeloid derived suppressor cells and lung tumors co-evolve in the course of disease inception and progression. In clinical NSCLC, numbers of circulating myeloid derived suppressor cells have been shown to inversely correlate with overall survival. M-MDSCs have been shown to produce reactive oxygen species, inhibit T-cell proliferation, and secrete interferon-γ (IFN-γ). Elevated levels of circulating myeloid derived suppressor cells and their activity inversely correlate with therapeutic response and positively correlate with relapse in NSCLC.

Non-Small Cell Lung Cancer

NSCLC is a cancer of the lung which is not of the small cell carcinoma (oat cell carcinoma) type. The term "non-small cell lung cancer" applies to the various types of bronchogenic carcinomas (those arising from the lining of the bronchi). Examples of specific types of NSCLC include, but are not limited to, adenocarcinoma, squamous cell carcinoma, and large cell cancer (i.e., large cell undifferentiated carcinoma).

Adenocarcinoma is a cancer that develops in the lining or inner surface of an organ. Adenocarcinoma is the most common type of lung cancer, making up 30%-40% of all cases of lung cancer. A subtype of adenocarcinoma is called bronchioalveolar cell carcinoma, which creates a pneumonia-like appearance on chest X-rays.

Squamous cell carcinoma is a cancer that begins in squamous cells. Squamos cells are thin, flat cells that look under the microscope like fish scales. Squamous cells are found in the tissue that forms the surface of the skin, the lining of hollow organs of the body, and the passages of the respiratory and digestive tracts. Squamous cell carcinomas may arise in any of these tissues. Squamous cell carcinoma is the second most common type of lung cancer, making up about 30% of all cases.

Large cell carcinoma shows no evidence of squamous or glandular maturation. Thus these tumors are often diagnosed by default, when all other possibilities have been excluded. These tumors lack any diagnostic features to suggest their diagnosis prior to biopsy. They tend to grow rapidly, metastasize early, and are strongly associated with smoking. Large cell tumors are usually large, bulky, well-circumscribed, pink-grey masses with extensive hemorrhage and necrosis. Although they commonly have central necrosis, they rarely cavitate. They tend to present in the mid to peripheral lung zones. They may extend locally to involve the segmental or subsegmental bronchi. A variant of large cell carcinoma is giant cell carcinoma. This subtype is particularly aggressive and carries a very poor prognosis. These tumors generally present as a large peripheral mass with a focal necrotic component. They do not involve the large airways, unless by direct extension. Large cell cancer makes up 10%-20% of all cases of lung cancer.

Melanoma

Melanoma is a malignant tumor of melanocytes, which are the cells that make the pigment melanin and are derived from the neural crest. Although most melanomas arise in the skin, they may also arise from mucosal surfaces or at other sites to which neural crest cells migrate, including the uveal tract. Uveal melanomas differ significantly from cutaneous melanoma in incidence, prognostic factors, molecular characteristics, and treatment.

In the United States in 2014, 9,710 people were projected to die from melanoma, and numbers of new cases were estimated to be 76,100. Skin cancer is the most common malignancy diagnosed in the United States, with 3.5 million cancers diagnosed in 2 million people annually. Melanoma represents less than 5% of skin cancers but results in most deaths. The incidence has been increasing over the past four decades. Elderly men are at highest risk; however, melanoma is the most common cancer in young adults aged 25 to 29 years and the second most common cancer in those aged 15 to 29 years. Ocular melanoma is the most common cancer of the eye, with approximately 2,000 cases diagnosed annually.

Melanoma occurs predominantly in adults, and more than 50% of the cases arise in apparently normal areas of the skin. Although melanoma can occur anywhere, including on mucosal surfaces and the uvea, melanoma in women occurs more commonly on the extremities, and in men it occurs most commonly on the trunk or head and neck.

Prognosis is affected by the characteristics of primary and metastatic tumors. The most important prognostic factors include, but are not limited to, the following: thickness or level of invasion of the melanoma, mitotic index, defined as mitoses per millimeter, ulceration or bleeding at the primary site, number of regional lymph nodes involved, with distinction of macrometastasis and micrometastasis, systemic metastasis, site—nonvisceral versus lung versus all other visceral sites, elevated serum lactate dehydrogenase level. Without being bound by any theory, it is contemplated that the presence of tumor infiltrating lymphocytes can be a potential prognostic factor.

Myeloid derived suppressor cells have been shown to have several important clinical correlations in melanoma. In the clinic, levels of circulating M-MDSCs and PMN-MDSCs positively correlate with disease burden in malignant melanoma. Patients with later-stage melanoma (stages 3-4) have higher levels of circulating M-MDSCs. Circulating levels of M-MDSCs are inversely correlated with overall survival in advanced melanoma. Circulating levels of M-MDSCs are further inversely correlated with reduced levels of activated antigen-specific T lymphocytes in patients with advanced melanoma. Decreased activation of M-MDSCs and PMN-MDSCs positively correlates with improved therapeutic response in melanoma patients treated with ipilumimab. Ipilumimab treatment has also been shown to reduce levels of circulating PMN-MDSCs.

Breast Cancer

Breast cancer is cancer that develops from breast tissue. Signs of breast cancer may include a lump in the breast, a change in breast shape, dimpling of the skin, fluid coming from the nipple, or a red scaly patch of skin. In those with distant spread of the disease, there may be bone pain, swollen lymph nodes, dyspnea, or jaundice. Outcomes for breast cancer vary depending on the cancer type, extent of disease, and subject age. Worldwide, breast cancer is the leading type of cancer in women, accounting for 25% of all cases. In 2012 it resulted in 1.68 million cases and 522,000 deaths. It is more common in developed countries and is more than 100 times more common in women than in men. Breast cancers are classified by several grading systems. Each of these systems can influence the prognosis and can affect treatment. Breast cancer is usually classified primarily by its histological appearance. Most breast cancers are derived from the epithelium lining the ducts or lobules, and these cancers are classified as ductal or lobular carcinoma. Carcinoma in situ is growth of low grade cancerous or precancerous cells within a particular tissue compartment such as the mammary duct without invasion of the surrounding tissue. In contrast, invasive carcinoma does not confine itself to the initial tissue compartment.

Breast cancer staging using the TNM system is based on the size of the tumor (T), whether or not the tumor has spread to the adjacent lymph nodes (N), and whether the tumor has metastasized (M) to a more distant part of the body. Larger size, nodal spread, and metastasis have a larger stage number and a worse prognosis. The main stages are stage 0, stages 1-3, and stage 4. Stage 0 is a pre-cancerous or marker condition, either ductal carcinoma in situ (DCIS) or lobular carcinoma in situ (LCIS). Stages 1-3 are within the breast or regional lymph nodes. Stage 4 is metastatic cancer that has a less favorable prognosis.

Breast cancer cells have receptors on their surface and in their cytoplasm and nucleus. Chemical messengers such as hormones bind to receptors, and this causes changes in the cell. Breast cancer cells can or cannot have three important receptors: estrogen receptor (ER), progesterone receptor (PR), and HER2. This leads to a division of breast cancers into hormone receptor-positive breast cancers or ER-/PR-positive breast cancers, HER2-positive breast cancers, and triple negative breast cancers, which are negative for ER, PR, and HER2.

Myeloid derived suppressor cells have been shown to have several important clinical correlations in breast cancer. In pre-clinical models of breast cancer, myeloid derived suppressor cell levels positively correlate with tumor size and inversely correlate with T cells. In the clinic, baseline levels of circulating myeloid derived suppressor cells correlate with disease burden, metastatic spread, and reduced survival in metastatic breast cancer. Baseline levels of circulating myeloid derived suppressor cells have been shown to correlate with response to adjuvant chemotherapy in HER2-negative breast cancer, with increasing levels indicating poorer response to chemotherapy.

Hormone Receptor-Positive Breast Cancer

Hormones, such as estrogen and progesterone, promote the growth of cancers that are hormone receptor-positive. About two out of three of breast cancers are hormone receptor-positive, as they contain receptors for the hormones estrogen (ER-positive breast cancers) or progesterone (PR-positive breast cancers). As these breast cancers depend upon the hormones for growth, therapies have been designed to either lower estrogen levels or stop estrogen activity breast cancer cells.

Non-limiting examples of therapies that stop estrogen activity include tamoxifen, toremifene, and fulvestrant. Tamoxifen blocks estrogen binding to estrogen receptors in breast cancer cells. While tamoxifen acts like an anti-estrogen in breast cells, it functions like an estrogen in other tissues, like the uterus and the bones. Because it acts like estrogen in some tissues but like an anti-estrogen in others, it is called a selective estrogen receptor modulator (SERM). Toremifene is another SERM that is approved to treat metastatic breast cancer. Fulvestrant is a drug that first blocks the estrogen receptor and triggers its degradation. Fulvestrant is not a SERM, as it acts like an anti-estrogen throughout the body. Fulvestrant is used to treat metastatic breast cancer after other hormone therapies, for example, tamoxifen, have stopped working.

Aromatase inhibitors (AIs) function to block estrogen production in post-menopausal women. Aromatase inhibitors work by blocking aromatase, which converts androgens generated by adipose tissue and the brain. Non-limiting examples of aromatase inhibitors include letrozole, anastrozole, and exemestane.

Triple Negative Breast Cancer

Triple-negative breast cancer, characterized by tumors that do not express estrogen receptor (ER), progesterone receptor (PR), or HER-2 genes, represents an important clinical challenge because these cancers do not respond to endocrine therapy or other available targeted agents. The metastatic potential in triple-negative breast cancer is similar to that of other breast cancer subtypes, but these tumors are associated with a shorter median time to relapse and death. One important goal is therefore the identification of prognostic factors and markers to reliably select high and low risk subsets of patients with triple-negative disease for different treatment approaches of subtypes with differential responsiveness to specific agents. However, a reliable prognostic marker has been elusive, and markers have been inconsistently useful. For example, epidermal growth factor receptor (EGFR) has been studied, but there is still a lack of agreement on a standard assay or cutoff for EGFR expression levels with respect to prognosis. Similarly, because triple-negative status is sometimes used as a surrogate for basal-like breast cancer, specific basal markers have been explored. Indeed, trials designed to accrue patients with basal-like breast cancer using ER/PR and HER-2 negativity may provide only an approximation of the triple-negative population and are sometimes reanalyzed using more specific indicators like CK 5/6, EGFR status, and others, again marred by discordances.

Chemotherapy remains the mainstay of treatment of triple-negative breast cancer, but important limitations still need to be overcome in the next few years if any significant clinical strides are to be made. Current treatment strategies for triple-negative disease include anthracyclines, taxanes, ixabepilone, platinum agents, and biologic agents. More recently, EGFR inhibition has been proposed as a therapeutic mechanism in triple-negative breast cancer, again with mixed results. Agents that target poly(ADP-ribose) polymerase and androgen receptors have also been proposed in these patients or subsets of them, and ongoing trials should result in definitive guidance with respect to the value of these agents in triple-negative disease. Triple-negative breast cancer is clearly a distinct clinical subtype, from the perspective of both ER and HER-2 expression, but further subclassification is needed. At present, there is not a clear, proven effective single agent that targets a defining vulnerability in triple-negative breast cancer.

Various subtypes of triple negative breast cancer includes basal like TNBC (Basal like 1 and 2 (BL-1, BL-2), Immunomodulatory (IM)) and mesenchymal stem like triple negative breast cancer (MSL), and luminal androgen receptor (LAR) subtype.

PD-L1 is expressed on many cancers including renal cell carcinoma, pancreatic cancer, ovarian cancer, gastric cancer, esophageal cancer, and hepatocellular carcinoma. Research has identified the expression of PD-L1 in 50% (22 out of 44 of tumors evaluated in a breast cancer study). In 15 (34%) it was restricted to the tumor epithelium, whereas in 18 (41%) it was identified in tumor infiltrating lymphocytes. Furthermore, it was found that intratumoral expression of PD-L1 was associated with high histologic grade and negative hormone receptor status. Consistent with the previous study, it was also in a separate study that approximately 20% of TNBC tumors express PD-L1. The majority (95%) of these TNBC tumors were grade 3.

Without being bound by any specific theory it is hypothesized that a possible mechanism by which tumors can drive PD-L1 expression is by oncogenic signaling pathways. This was first demonstrated in glioblastomas where it was observed that PTEN loss was associated with increased PD-L1 expression, suggesting the involvement of the PI3K pathway. Because PTEN loss is commonly seen in TNBC, a study investigated the relationship between PTEN and PD-L1 expression. In approximately 50% of TNBC tumors included in the breast cancer tissue microarrays where there was >5% PD-L1 expression, a loss of PTEN staining was observed. Similarly, in a panel of TNBC cell lines, it was found that two exemplary cell lines with PTEN loss, MDA-MB-468 and BT-549, had high cell surface PD-L1 expression. Together, these data suggested that there are likely multiple mechanisms of PD-L1 regulation in TNBC.

Methods of Selecting Patients for Combination Therapy

In certain embodiments, a method of the present disclosure comprises measuring myeloid derived suppressor cells and peripheral blood mononuclear cells to determine administration of a combination therapy comprising entinostat and a second therapeutic agent to a patient diagnosed with a cancer. In some embodiments, the method further comprises selecting the patient for combination therapy if the ratio of myeloid derived suppressor to peripheral blood mononuclear cells is between 1:200 and 1:4.

In certain embodiments, a method of the present disclosure comprises measuring CD14-positive and HLA-DR-(lo/negative) cells, measuring CD14-positive cells, or measuring peripheral blood mononuclear cells to determine administration of a combination therapy comprising entinostat and a second therapeutic agent to a patient diagnosed with a cancer. In some embodiments, the method further comprises selecting the patient for combination therapy if the ratio of CD14-positive and HLA-DR-(lo/negative) cells to peripheral blood mononuclear cells is between 1:200 and 1:1. In some embodiments, the method further comprises selecting the patient for combination therapy if the ratio of CD14-positive and HLA-DR-(lo/negative) cells to CD14-positive cells is between 1:100 and 99:1.

Non-limiting examples of the second therapeutic agent include anti-PD-1 antibodies, for example, nivolumab and pembrolizumab; anti-PD-L1 antibodies, such as MPDL3280A; and exemestane. Non-limiting examples of the cancer include breast cancers, for example, hormone receptor-positive breast cancers and triple negative breast cancers; lung cancers, for example, non-small cell lung cancers, squamous cell carcinomas, and large cell carcinomas; and melanomas, for example, metastatic melanomas. In some embodiments, the second therapeutic agent is MPDL3280A and the cancer is a breast cancer. In some embodiments, the second therapeutic agent is MPDL3280A and the breast cancer is a triple-negative breast cancer. In some embodiments, the second therapeutic agent is exemestane and the cancer is a breast cancer. In some embodiments, the second therapeutic agent is exemestane and the breast cancer is a hormone receptor-positive breast cancer.

In some embodiments, the entinostat and exemestane are administered orally. In some embodiments, the entinostat is administered orally and the anti-PD-1 antibody or anti-PD-L1 antibody is administered by an infusion. Non-limiting examples of infusions include subcutaneous infusion, intravenous infusion, intraperitoneal infusion, and infusion by osmotic pump.

In some embodiments, the entinostat is administered first in the combination therapy. In some embodiments, the entinostat is administered weekly. In some embodiments, the entinostat is administered every two weeks.

Entinostat, exemestane, anti-PD-1 antibody, or anti-PD-L1 antibody can be administered about every day, about every two days, about every three days, about every four days, about every five days, about every six days, about every week, about every two weeks, about every three weeks, about every four weeks, about every month, about every five weeks, about every six weeks, about every seven weeks, about every eight weeks, or about every two months. Entinostat, exemestane, anti-PD-1 antibody, or anti-PD-L1 antibody can be administered from about every day to about every two days, from about every two days to about every three days, from about every three days to about every four days, from about every four days to about every five days, from about every five days to about every six days, from about every six days to about every week, from about every week to about every two weeks, from about every two weeks to about every three weeks, from about every three weeks to about every four weeks, from about every four weeks to about every month, from about every month to about every five weeks, from about every five weeks to about every six weeks, from about every six weeks to about every seven weeks, from about every seven weeks to about every eight weeks, or from about every eight weeks to about every two months.

In some embodiments, the myeloid derived suppressor cells and peripheral blood mononuclear cells are circulating and are each measured in peripheral blood by obtaining a peripheral blood sample. In some embodiments, the CD14-positive and HLA-DR-(lo/negative) cells, CD14-positive cells, and peripheral blood mononuclear cells are circulating and are each measured in peripheral blood by obtaining a peripheral blood sample. In some embodiments, the peripheral blood sample is treated with an anticoagulant. In some embodiments, the peripheral blood sample is collected in or transferred into an anticoagulant-containing container. Non-limiting examples of anticoagulants include heparin, sodium heparin, potassium oxalate, EDTA, and sodium citrate. In some embodiments, the peripheral blood sample is treated with a red blood cell lysis agent. In some embodiments, the myeloid derived suppressor cells and peripheral blood mononuclear cells are measured in tissue biopsies.

In some embodiments, a number of myeloid derived suppressor cells and peripheral blood mononuclear cells are measured in the peripheral blood sample and a percentage of myeloid derived suppressor cells relative to peripheral blood mononuclear cells is determined. In some embodiments, one or more myeloid derived suppressor cells from the peripheral blood sample is contacted with a first binding agent to generate one or more first binding agent-myeloid derived suppressor cell complexes. In some embodiments, one or more peripheral blood mononuclear cells from the peripheral blood sample is contacted with a second binding agent to generate one or more second binding agent-peripheral blood mononuclear cell complexes. In some embodiments, a percentage of the first binding agent-myeloid derived suppressor cell complexes relative to the second binding agent-peripheral blood mononuclear cell complexes in the peripheral blood sample is measured.

In some embodiments, the percentage of myeloid derived suppressor cells relative to peripheral blood mononuclear cells, or that of first binding agent-myeloid derived suppressor cell complexes and the second binding agent-peripheral blood mononuclear cell complexes, in a peripheral blood sample or a tissue biopsy is utilized to select patients for administering a combination therapy comprising entinostat and a second therapeutic agent.

In some embodiments, the percentage of myeloid derived suppressor or peripheral blood mononuclear cells, or that of first binding agent-myeloid derived suppressor cell complexes and the second binding agent-peripheral blood mononuclear cell complexes, in a peripheral blood sample or a tissue biopsy is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 30%, at least about 35%, at least about 40%, at least about 45%, or at least about 50%.

In some embodiments, the percentage of myeloid derived suppressor cells relative to peripheral blood mononuclear cells, or that of first binding agent-myeloid derived suppressor cell complexes and the second binding agent-peripheral blood mononuclear cell complexes, in a peripheral blood sample or a tissue biopsy myeloid derived suppressor cells is from about 0.1% to about 0.2%, from about 0.2% to about 0.3%, from about 0.3% to about 0.4%, from about 0.4% to about 0.5%, from about 0.5% to about 0.6%, from about 0.6% to about 0.7%, from about 0.7% to about 0.8%, from about 0.8% to about 0.9%, from about 0.9% to about 1%, from about 1% to about 1.1%, from about 1.1% to about 1.2%, from about 1.2% to about 1.3%, from about 1.4% to about 1.5%, from about 1.5% to about 1.6%, from about 1.6% to about 1.7%, from about 1.7% to about 1.8%, from about 1.8% to about 1.9%, from about 1.9% to about 2%, from about 2% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, from about 11% to about 12%, from about 12% to about 13%, from about 13% to about 14%, from about 14% to about 15%, from about 15% to about 16%, from about 16% to about 17%, from about 17% to about 18%, from about 18% to about 19%, from about 19% to about 20%, from about 20% to about 21%, from about 21% to about 22%, from about 22% to about 23%, from about 23% to about 24%, from about 24% to about 25%, from about 25% to about 30%, from about 30% to about 35%, from about 35% to about 40%, from about 40% to about 45%, or from about 45% to about 50%.

In some embodiments, a number of myeloid derived suppressor cells and peripheral blood mononuclear cells are measured in the peripheral blood sample and a ratio of myeloid derived suppressor cells to peripheral blood mononuclear cells is determined. In some embodiments, one or more myeloid derived suppressor cells from the peripheral blood sample is contacted with a first binding agent to generate one or more first binding agent-myeloid derived suppressor cell complexes. In some embodiments, one or more peripheral blood mononuclear cells from the peripheral blood sample is contacted with a second binding agent to generate one or more second binding agent-peripheral blood mononuclear cell complexes. In some embodiments, a ratio of the first binding agent-myeloid derived suppressor cell complexes and the second binding agent-peripheral blood mononuclear cell complexes in the peripheral blood sample is measured. In some embodiments, the ratio of myeloid derived suppressor cells to peripheral blood mononuclear cells, or that of first binding agent-myeloid derived suppressor cell complexes and the second binding agent-peripheral blood mononuclear cell complexes, is utilized to select patients for administering a combination therapy comprising entinostat and a second therapeutic agent.

In some embodiments, the ratio of first binding agent-myeloid derived suppressor cell complexes and the second binding agent-peripheral blood mononuclear cell complexes utilized to select patients for administering a combination therapy comprising entinostat and a second therapeutic agent.

In some embodiments, the ratio of myeloid derived suppressor cells relative to peripheral blood mononuclear cells, or that of first binding agent-myeloid derived suppressor cell complexes and the second binding agent-peripheral blood mononuclear cell complexes in a peripheral blood sample or a tissue biopsy is 1:10000, 1:5000, 1:4000, 1:3000, 1:2000, 1:1000, 1:500, 1:400, 1:300, 1:250, 1:200, 1:150, 1:100, 1:90, 1:80, 1:70, 1:60, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, or 1:1.

In some embodiments, the ratio of myeloid derived suppressor cells relative to peripheral blood mononuclear cells, or that of first binding agent-myeloid derived suppressor cell complexes and the second binding agent-peripheral blood mononuclear cell complexes in a peripheral blood sample or a tissue biopsy is from 1:10000 to 1:5000, from 1:5000 to 1:4000, from 1:4000 to 1:3000, from 1:3000 to 1:2000, from 1:2000 to 1:1000, from 1:1000 to 1:500, from 1:500 to 1:400, from 1:400 to 1:300, from 1:300 to 1:200, from 1:200 to 1:100, from 1:100 to 1:90, from 1:90 to 1:80, from 1:80 to 1:70, from 1:70 to 1:60, from 1:60 to 1:50, from 1:50 to 1:49, from 1:49 to 1:48, from 1:48 to 1:47, from 1:47 to 1:46, from 1:46 to 1:45, from 1:45 to 1:44, from 1:44 to 1:43, from 1:43 to 1:42, from 1:42 to 1:41, from 1:41 to 1:40, from 1:40 to 1:39, from 1:39 to 1:38, from 1:38 to 1:37, from 1:37 to 1:36, from 1:36 to 1:35, from 1:35 to 1:34, from 1:34 to 1:33, from 1:33 to 1:32, from 1:32 to 1:31, from 1:31 to 1:30, from 1:30 to 1:29, from 1:29 to 1:28, from 1:28 to 1:27, from 1:27 to 1:26, from 1:26 to 1:25, from 1:25 to 1:24, from 1:24 to 1:23, from 1:23 to 1:22, from 1:22 to 1:21, from 1:21 to 1:20, from 1:20 to 1:19, from 1:19 to 1:18, from 1:18 to 1:17, from 1:17 to 1:16, from 1:16 to 1:15, from 1:15 to 1:14, from 1:14 to 1:13, from 1:13 to 1:12, from 1:12 to 1:11, from 1:11 to 1:10, from 1:10 to 1:9, from 1:9 to 1:8, from 1:8 to 1:7, from 1:7 to 1:6, from 1:6 to 1:5, from 1:5 to 1:4, from 1:4 to 1:3, from 1:3 to 1:2, or from 1:2 to 1:1.

In some embodiments, a number of myeloid derived suppressor cells per unit volume of a biological sample is determined. Non-limiting examples of unit volumes include picoliters (pL), nanoliters (nL), microliters (4), milliliters (mL), deciliters (dL), and liters (L). In some embodiments, a number of myeloid derived suppressor cells from the peripheral blood sample is contacted with a binding agent to generate a number of binding agent-myeloid derived suppressor cell complexes per unit volume. In some embodiments, the number of myeloid derived suppressor cells or binding agent-myeloid derived suppressor cell complexes per unit volume of the biological sample utilized to select patients for administering a combination therapy comprising entinostat and a second therapeutic agent. In some embodiments, the biological sample is peripheral blood sample.

In some embodiments, the myeloid derived suppressor cells or binding agent-myeloid derived suppressor cell complexes per unit volume of the biological sample is about 1, about 2, about 3, about 4, about 5, about 6, about 7, about 8, about 9, about 10, about 15, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1500, about 2000, about 2500, about 3000, about 3500, about 4000, about 4500, about 5000, about 6000, about 7000, about 8000, about 9000, about 10000, about 15000, about 20000, about 25000, about 30000, about 35000, about 40000, about 45000, about 50000, about 60000, about 70000, about 80000, about 90000, or about 100000 per unit volume.

In some embodiments, the myeloid derived suppressor cells or binding agent-myeloid derived suppressor cell complexes per unit volume of the biological sample is from about 1 to about 2, from about 2 to about 3, from about 3 to about 4, from about 4 to about 5, from about 5 to about 6, from about 6 to about 7, from about 7 to about 8, from about 8 to about 9, from about 9 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, from about 450 to about 500, from about 500 to about 600, from about 600 to about 700, from about 700 to about 800, from about 800 to about 900, from about 900 to about 1000, from about 1000 to about 1500, from about 1500 to about 2000, from about 2000 to about 2500, from about 2500 to about 3000, from about 3000 to about 3500, from about 3500 to about 4000, from about 4000 to about 4500, from about 4500 to about 5000, from about 5000 to about 6000, from about 6000 to about 7000, from about 7000 to about 8000, from about 8000 to about 9000, from about 9000 to about 10000, from about 10000 to about 15000, from about 15000 to about 20000, from about 20000 to about 25000, from about 25000 to about 30000, from about 30000 to about 35000, from about 35000 to about 40000, from about 40000 to about 45000, from about 45000 to about 50000, from about 50000 to about 60000, from about 60000 to about 70000, from about 70000 to about 80000, from about 80000 to about 90000, or from about 90000 to about 100000 per unit volume.

In some embodiments, a number of CD14-positive and HLA-DR-(lo/negative) cells, CD14-positive cells, and peripheral blood mononuclear cells are measured in the peripheral blood sample and a percentage of CD14-positive and HLA-DR-(lo/negative) cells, CD14-positive cells, and peripheral blood mononuclear cells is determined.

In some embodiments, the percentage of CD14-positive and HLA-DR-(lo/negative) cells relative to either CD14-positive cells or peripheral blood mononuclear cells is utilized to select patients for administering a combination therapy comprising entinostat and a second therapeutic agent.

In some embodiments, the percentage of CD14-positive and HLA-DR-(lo/negative) cells relative to either CD14-positive cells or peripheral blood mononuclear cells in a peripheral blood sample or a tissue biopsy is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 30%, at least about 35%, at least about 40%, at least about 45%, at least about 50%, at least about 60%, at least about 70%, at least about 80%, at least about 90%, at least about 95%, at least about 96%, at least about 97%, at least about 98%, or at least about 99%.

In some embodiments, the percentage of CD14-positive and HLA-DR-(lo/negative) cells relative to either CD14-positive cells or peripheral blood mononuclear cells in a peripheral blood sample or a tissue biopsy is from about 0.1% to about 0.2%, from about 0.2% to about 0.3%, from about 0.3% to about 0.4%, from about 0.4% to about 0.5%, from about 0.5% to about 0.6%, from about 0.6% to about 0.7%, from about 0.7% to about 0.8%, from about 0.8% to about 0.9%, from about 0.9% to about 1%, from about 1% to about 1.1%, from about 1.1% to about 1.2%, from about 1.2% to about 1.3%, from about 1.4% to about 1.5%, from about 1.5% to about 1.6%, from about 1.6% to about 1.7%, from about 1.7% to about 1.8%, from about 1.8% to about 1.9%, from about 1.9% to about 2%, from about 2% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, from about 11% to about 12%, from about 12% to about 13%, from about 13% to about 14%, from about 14% to about 15%, from about 15% to about 16%, from about 16% to about 17%, from about 17% to about 18%, from about 18% to about 19%, from about 19% to about 20%, from about 20% to about 21%, from about 21% to about 22%, from about 22% to about 23%, from about 23% to about 24%, from about 24% to about 25%, from about 25% to about 30%, from about 30% to about 35%, from about 35% to about 40%, from about 40% to about 45%, from about 45% to about 50%, from about 50% to about 60%, from about 60% to about 70%, from about 70% to about 80%, from about 80% to about 90%, from about 90% to about 95%, from about 95% to about 96%, from about 96% to about 97%, from about 97% to about 98%, or from about 98% to about 99%.

In some embodiments, a number of CD14-positive and HLA-DR-(lo/negative) cells, CD14-positive cells, and peripheral blood mononuclear cells are measured in the peripheral blood sample and a ratio of CD14-positive and HLA-DR-(lo/negative) cells relative to either CD14-positive cells or peripheral blood mononuclear cells is determined. In some embodiments, the ratio of CD14-positive and HLA-DR-(lo/negative) cells relative to either CD14-positive cells or peripheral blood mononuclear cells is utilized to select patients for administering a combination therapy comprising entinostat and a second therapeutic agent.

In some embodiments, the ratio of CD14-positive and HLA-DR-(lo/negative) cells relative to either CD14-positive cells or peripheral blood mononuclear cells in a peripheral blood sample or a tissue biopsy is 1:10000, 1:5000, 1:4000, 1:3000, 1:2000, 1:1000, 1:500, 1:400, 1:300, 1:250, 1:200, 1:150, 1:100, 1:90, 1:80, 1:70, 1:60, 1:50, 1:49, 1:48, 1:47, 1:46, 1:45, 1:44, 1:43, 1:42, 1:41, 1:40, 1:39, 1:38, 1:37, 1:36, 1:35, 1:34, 1:33, 1:32, 1:31, 1:30, 1:29, 1:28, 1:27, 1:26, 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 9:1, 19:1, 24:1, 97:1, 49:1, or 99:1.

In some embodiments, the ratio of CD14-positive and HLA-DR-(lo/negative) cells relative to either CD14-positive cells or peripheral blood mononuclear cells in a peripheral blood sample or a tissue biopsy is from 1:10000 to 1:5000, from 1:5000 to 1:4000, from 1:4000 to 1:3000, from 1:3000 to 1:2000, from 1:2000 to 1:1000, from 1:1000 to 1:500, from 1:500 to 1:400, from 1:400 to 1:300, from 1:300 to 1:200, from 1:200 to 1:100, from 1:100 to 1:90, from 1:90 to 1:80, from 1:80 to 1:70, from 1:70 to 1:60, from 1:60 to 1:50, from 1:50 to 1:49, from 1:49 to 1:48, from 1:48 to 1:47, from 1:47 to 1:46, from 1:46 to 1:45, from 1:45 to 1:44, from 1:44 to 1:43, from 1:43 to 1:42, from 1:42 to 1:41, from 1:41 to 1:40, from 1:40 to 1:39, from 1:39 to 1:38, from 1:38 to 1:37, from 1:37 to 1:36, from 1:36 to 1:35, from 1:35 to 1:34, from 1:34 to 1:33, from 1:33 to 1:32, from 1:32 to 1:31, from 1:31 to 1:30, from 1:30 to 1:29, from 1:29 to 1:28, from 1:28 to 1:27, from 1:27 to 1:26, from 1:26 to 1:25, from 1:25 to 1:24, from 1:24 to 1:23, from 1:23 to 1:22, from 1:22 to 1:21, from 1:21 to 1:20, from 1:20 to 1:19, from 1:19 to 1:18, from 1:18 to 1:17, from 1:17 to 1:16, from 1:16 to 1:15, from 1:15 to 1:14, from 1:14 to 1:13, from 1:13 to 1:12, from 1:12 to 1:11, from 1:11 to 1:10, from 1:10 to 1:9, from 1:9 to 1:8, from 1:8 to 1:7, from 1:7 to 1:6, from 1:6 to 1:5, from 1:5 to 1:4, from 1:4 to 1:3, from 1:3 to 1:2, from 1:2 to 1:1, from 1:1 to 2:1, from 2:1 to 3:1, from 3:1 to 4:1, from 4:1 to 9:1, from 9:1 to 19:1, from 19:1 to 24:1, from 24:1 to 97:1, from 97:1 to 49:1, or from 49:1 to 99:1.

In some embodiments, a number of CD14-positive and HLA-DR-(lo/negative) cells per unit volume of a biological sample is determined. Non-limiting examples of unit volumes include picoliters (pL), nanoliters (nL), microliters (4), milliliters (mL), deciliters (dL), and liters (L). In some embodiments, the number of CD14-positive and HLA-DR-(lo/negative) cells per unit volume of the biological sample is utilized to select patients for administering a combination therapy comprising entinostat and a second therapeutic agent. In some embodiments, the biological sample is peripheral blood sample.

In some embodiments, the number of CD14-positive and HLA-DR-(lo/negative) cells per unit volume of the biological sample is about 1, about 2, about 3, about 4, about 5, about 6, about 7, about 8, about 9, about 10, about 15, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1500, about 2000, about 2500, about 3000, about 3500, about 4000, about 4500, about 5000, about 6000, about 7000, about 8000, about 9000, about 10000, about 15000, about 20000, about 25000, about 30000, about 35000, about 40000, about 45000, about 50000, about 60000, about 70000, about 80000, about 90000, or about 100000 per unit volume.

In some embodiments, the number of CD14-positive and HLA-DR-(lo/negative) cells per unit volume of the biological sample is from about 1 to about 2, from about 2 to about 3, from about 3 to about 4, from about 4 to about 5, from about 5 to about 6, from about 6 to about 7, from about 7 to about 8, from about 8 to about 9, from about 9 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, from about 450 to about 500, from about 500 to about 600, from about 600 to about 700, from about 700 to about 800, from about 800 to about 900, from about 900 to about 1000, from about 1000 to about 1500, from about 1500 to about 2000, from about 2000 to about 2500, from about 2500 to about 3000, from about 3000 to about 3500, from about 3500 to about 4000, from about 4000 to about 4500, from about 4500 to about 5000, from about 5000 to about 6000, from about 6000 to about 7000, from about 7000 to about 8000, from about 8000 to about 9000, from about 9000 to about 10000, from about 10000 to about 15000, from about 15000 to about 20000, from about 20000 to about 25000, from about 25000 to about 30000, from about 30000 to about 35000, from about 35000 to about 40000, from about 40000 to about 45000, from about 45000 to about 50000, from about 50000 to about 60000, from about 60000 to about 70000, from about 70000 to about 80000, from about 80000 to about 90000, or from about 90000 to about 100000 per unit volume.

In some embodiments, myeloid derived suppressor cells, CD14-positive and HLA-DR-(lo/negative) cells, CD14-positive cells, and/or peripheral blood mononuclear cells are measured using flow cytometry, mass cytometry, cytospin, or immunohistochemistry.

Flow cytometry is a laser-based technology used in cell counting, cell sorting, and biomarker detection, by suspending cells in a stream of fluid and passing them by an electronic detection apparatus. It allows simultaneous multiparametric analysis of the physical and chemical characteristics of up to thousands of particles per second.

Mass cytometry is a mass spectrometry technique based on inductively coupled plasma mass spectrometry for the determination cell identity and function. In this technology, binding agents are tagged with isotopically pure rare earth elements. These binding agents are then applied to tag cells and their components. Cells are nebulized and sent through an argon plasma laser, ionizing the multi-atom rare earth elemental tags. The ionized, tagged cells are then analyzed by a time-of-flight mass spectrometer. The advantage of mass cytometry is the capacity to overcome the limitations developed by spectral overlap in flow cytometry.

Cytospin is a technique in which suspension cells are centrifuged onto glass slides as a smear for cell staining and cell counting. Concentrated cell suspensions that exist in a low-viscosity medium make good candidates for smear preparations. Dilute cell suspensions existing in a dilute medium are best suited for the preparation of cytospins through cytocentrifugation. Cell suspensions that exist in a high-viscosity medium, are best suited to be tested as swab preparations. The constant among these preparations is that the whole cell is present on the slide surface. Immunohistochemistry is a type of histological staining for detecting antigens in cells of a tissue section by exploiting the principle of antibodies binding specifically to antigens in biological tissues. Visualizing an antibody-antigen interaction can be accomplished in a number of ways. The antibody can be conjugated to an enzyme, such as peroxidase, that can catalyze a color-producing reaction. Alternatively, the antibody can be tagged to a fluorophore, such as fluorescein or rhodamine.

In some embodiments, flow cytometry, mass cytometry, cytospin, or immunohistochemistry is used to detect cells such as myeloid derived suppressor cells or peripheral blood mononuclear cells. In some embodiments, flow cytometry, mass cytometry, cytospin, or immunohistochemistry include use of a binding agent to create a binding agent-myeloid derived suppressor cells and a binding agent-peripheral blood mononuclear cells complex. In some embodiments, the binding agent is used to identify myeloid derived suppressor cells and peripheral blood mononuclear cells by a cell surface marker. In some embodiments, the binding agent is an antibody.

In some embodiments, the number of binding agents bound to a myeloid derived suppressor cell or peripheral blood mononuclear cell is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 20, least about 30, least about 40, at least about 50, at least about 60, at least about 70, least about 80, least about 90, at least about 100, at least about 125, at least about 150, at least about 175, or at least about 200. In some embodiments, the number of binding agents bound to a myeloid derived suppressor cell or peripheral blood mononuclear cell is from about 1 to about 2, from about 2 to about 3, from about 3 to about 4, from about 4 to about 5, from about 5 to about 6, from about 6 to about 7, from about 7 to about 8, from about 8 to about 9, from about 9 to about 10, from about 10 to about 11, from about 11 to about 12, from about 12 to about 13, from about 14 to about 15, from about 15 to about 16, from about 16 to about 20, from about 20 to about 30, from about 30 to about 40, from about 40 to about 50, from about 50 to about 60, from about 60 to about 70, from about 70 to about 80, from about 80 to about 90, from about 90 to about 100, from about 100 to about 125, from about 125 to about 150, from about 150 to about 175, or from about 175 to about 200.

In some embodiments, myeloid derived suppressor cells and peripheral blood mononuclear cells, M-MDSCs, or PMN-MDSCs are identified by a cell surface marker. Non-limiting examples of cell surface markers that identify myeloid derived suppressor cells include CD11b, CD33, and CD40. Non-limiting examples of cell surface markers that identify peripheral blood mononuclear cells include CD3, CD14, CD19, CD56, and HLA-DR. M-MDSCs can be identified by any combination of the myeloid derived suppressor cell markers combined with CD14. PMN-MDSCs can be identified by any combination of the myeloid derived suppressor cell markers combined with CD15. In some embodiments, the myeloid derived suppressor cells, peripheral blood mononuclear cells, M-MDSCs, or PMN-MDSCs are contacted by a binding agent to form a cell-binding agent complex. The binding agent can bind any of the foregoing cell surface markers or any combination thereof.

In some embodiments, myeloid derived suppressor cells are identified by CD11b and peripheral blood mononuclear cells are identified by CD3. In some embodiments, myeloid derived suppressor cells are identified by CD11b and Peripheral blood mononuclear cells are identified by CD14. In some embodiments, myeloid derived suppressor cells are identified by CD11b and peripheral blood mononuclear cells are identified by CD19. In some embodiments, myeloid derived suppressor cells are identified by CD11b and peripheral blood mononuclear cells are identified by CD56. In some embodiments, myeloid derived suppressor cells are identified by CD11b and peripheral blood mononuclear cells are identified by HLA-DR. In some embodiments, myeloid derived suppressor cells are identified by CD33 and peripheral blood mononuclear cells are identified by CD3. In some embodiments, myeloid derived suppressor cells are identified by CD33 and peripheral blood mononuclear cells are identified by CD14. In some embodiments, myeloid derived suppressor cells are identified by CD33 and peripheral blood mononuclear cells are identified by CD19. In some embodiments, myeloid derived suppressor cells are identified by CD33 and peripheral blood mononuclear cells are identified by CD56. In some embodiments, myeloid derived suppressor cells are identified by CD33 and peripheral blood mononuclear cells are identified by HLA-DR. In some embodiments, myeloid derived suppressor cells are identified by CD40 and peripheral blood mononuclear cells are identified by CD3. In some embodiments, myeloid derived suppressor cells are identified by CD40 and peripheral blood mononuclear cells are identified by CD14. In some embodiments, myeloid derived suppressor cells are identified by CD40 and peripheral blood mononuclear cells are identified by CD19. In some embodiments, myeloid derived suppressor cells are identified by CD40 and peripheral blood mononuclear cells are identified by CD56. In some embodiments, myeloid derived suppressor cells are identified by CD40 and peripheral blood mononuclear cells are identified by HLA-DR. In some embodiments, myeloid derived suppressor cells are identified by CD11b and CD33 and peripheral blood mononuclear cells are identified by CD3. In some embodiments, myeloid derived suppressor cells are identified by CD11b and CD33 and peripheral blood mononuclear cells are identified by CD14. In some embodiments, myeloid derived suppressor cells are identified by CD11b and CD33 and peripheral blood mononuclear cells are identified by CD19. In some embodiments, myeloid derived suppressor cells are identified by CD11b and CD33 and peripheral blood mononuclear cells are identified by CD56. In some embodiments, myeloid derived suppressor cells are identified by CD11b and CD33 and peripheral blood mononuclear cells are identified by HLA-DR. In some embodiments, myeloid derived suppressor cells are identified by CD11b and CD33 and peripheral blood mononuclear cells are identified by CD3, CD14, CD19, CD56, and HLA-DR.

In some embodiments, M-MDSCs are identified by CD11b and CD14 and peripheral blood mononuclear cells are identified by CD3. In some embodiments, M-MDSCs are identified by CD11b and CD14 and peripheral blood mononuclear cells are identified by CD14. In some embodiments, M-MDSCs are identified by CD11b and CD14 and peripheral blood mononuclear cells are identified by CD19. In some embodiments, M-MDSCs are identified by CD11b and CD14 and peripheral blood mononuclear cells are identified by CD56. In some embodiments, M-MDSCs are identified by CD11b and CD14 and peripheral blood mononuclear cells are identified by HLA-DR. In some embodiments, M-MDSCs are identified by CD33 and CD14 and peripheral blood mononuclear cells are identified by CD3. In some embodiments, M-MDSCs are identified by CD33 and CD14 and peripheral blood mononuclear cells are identified by CD14. In some embodiments, M-MDSCs are identified by CD33 and CD14 and peripheral blood mononuclear cells are identified by CD19. In some embodiments, M-MDSCs are identified by CD33 and CD14 and peripheral blood mononuclear cells are identified by CD56. In some embodiments, M-MDSCs are identified by CD33 and CD14 and peripheral blood mononuclear cells are identified by HLA-DR. In some embodiments, M-MDSCs are identified by CD40 and CD14 and peripheral blood mononuclear cells are identified by CD3. In some embodiments, M-MDSCs are identified by CD40 and CD14 and peripheral blood mononuclear cells are identified by CD14. In some embodiments, M-MDSCs are identified by CD40 and CD14 and peripheral blood mononuclear cells are identified by CD19. In some embodiments, M-MDSCs are identified by CD40 and CD14 and peripheral blood mononuclear cells are identified by CD56. In some embodiments, M-MDSCs are identified by CD40 and CD14 and peripheral blood mononuclear cells are identified by HLA-DR. In some embodiments, M-MDSCs are identified by CD11b and CD33 and CD14 and peripheral blood mononuclear cells are identified by CD3. In some embodiments, M-MDSCs are identified by CD11b and CD33 and CD14 and peripheral blood mononuclear cells are identified by CD14. In some embodiments, M-MDSCs are identified by CD11b and CD33 and CD14 and peripheral blood mononuclear cells are identified by CD19. In some embodiments, M-MDSCs are identified by CD11b and CD33 and CD14 and peripheral blood mononuclear cells are identified by CD56. In some embodiments, M-MDSCs are identified by CD11b and CD33 and CD14 and peripheral blood mononuclear cells are identified by HLA-DR. In some embodiments, M-MDSCs are identified by CD11b and CD33 and CD14 and peripheral blood mononuclear cells are identified by CD3, CD14, CD19, CD56, and HLA-DR.

In some embodiments, PMN-MDSCs are identified by CD11b and CD15 and peripheral blood mononuclear cells are identified by CD3. In some embodiments, PMN-MDSCs are identified by CD11b and CD15 and peripheral blood mononuclear cells are identified by CD14. In some embodiments, PMN-MDSCs are identified by CD11b and CD15 and peripheral blood mononuclear cells are identified by CD19. In some embodiments, PMN-MDSCs are identified by CD11b and CD15 and peripheral blood mononuclear cells are identified by CD56. In some embodiments, PMN-MDSCs are identified by CD11b and CD15 and peripheral blood mononuclear cells are identified by HLA-DR. In some embodiments, PMN-MDSCs are identified by CD33 and CD15 and peripheral blood mononuclear cells are identified by CD3. In some embodiments, PMN-MDSCs are identified by CD33 and CD15 and peripheral blood mononuclear cells are identified by CD14. In some embodiments, PMN-MDSCs are identified by CD33 and CD15 and peripheral blood mononuclear cells are identified by CD19. In some embodiments, PMN-MDSCs are identified by CD33 and CD15 and peripheral blood mononuclear cells are identified by CD56. In some embodiments, PMN-MDSCs are identified by CD33 and CD15 and peripheral blood mononuclear cells are identified by HLA-DR. In some embodiments, PMN-MDSCs are identified by CD40 and CD15 and peripheral blood mononuclear cells are identified by CD3. In some embodiments, PMN-MDSCs are identified by CD40 and CD15 and peripheral blood mononuclear cells are identified by CD14. In some embodiments, PMN-MDSCs are identified by CD40 and CD15 and peripheral blood mononuclear cells are identified by CD19. In some embodiments, PMN-MDSCs are identified by CD40 and CD15 and peripheral blood mononuclear cells are identified by CD56. In some embodiments, PMN-MDSCs are identified by CD40 and CD15 and peripheral blood mononuclear cells are identified by HLA-DR. In some embodiments, PMN-MDSCs are identified by CD11b and CD33 and CD15 and Peripheral blood mononuclear cells are identified by CD3. In some embodiments, PMN-MDSCs are identified by CD11b and CD33 and CD15 and peripheral blood mononuclear cells are identified by CD14. In some embodiments, PMN-MDSCs are identified by CD11b and CD33 and CD15 and peripheral blood mononuclear cells are identified by CD19. In some embodiments, PMN-MDSCs are identified by CD11b and CD33 and CD15 and peripheral blood mononuclear cells are identified by CD56. In some embodiments, PMN-MDSCs are identified by CD11b and CD33 and CD15 and peripheral blood mononuclear cells are identified by HLA-DR. In some embodiments, PMN-MDSCs are identified by CD11b and CD33 and CD15 and peripheral blood mononuclear cells are identified by CD3, CD14, CD19, CD56, and HLA-DR.

In some embodiments, PMN-MDSCs cells are identified by CD11b an absence of CD14 on the cell surface and peripheral blood mononuclear cells are identified by CD3. In some embodiments, PMN-MDSCs are identified by CD11b an absence of CD14 on the cell surface and peripheral blood mononuclear cells are identified by CD14. In some embodiments, PMN-MDSCs are identified by CD11 an absence of CD14 on the cell and peripheral blood mononuclear cells are identified by CD19. In some embodiments, PMN-MDSCs are identified by CD11b14 an absence of CD14 on the cell surface and peripheral blood mononuclear cells are identified by CD56. In some embodiments, PMN-MDSCs cells are identified by CD11b an absence of CD14 on the cell surface and peripheral blood mononuclear cells are identified by HLA-DR. In some embodiments, PMN-MDSCs cells are identified by CD33 an absence of CD14 on the cell surface and peripheral blood mononuclear cells are identified by CD3. In some embodiments, PMN-MDSCs are identified by CD33 and an absence of CD14 on the cell surface and peripheral blood mononuclear cells are identified by CD14. In some embodiments, PMN-MDSCs are identified by CD33 and an absence of CD14 on the cell surface and peripheral blood mononuclear cells are identified by CD19. In some embodiments, PMN-MDSCs are identified by CD33 and an absence of CD14 on the cell surface and peripheral blood mononuclear cells are identified by CD56. In some embodiments, PMN-MDSCs are identified by CD33 and an absence of CD14 on the cell surface and peripheral blood mononuclear cells are identified by HLA-DR. In some embodiments, PMN-MDSCs are identified by CD40 and an absence of CD14 on the cell surface and peripheral blood mononuclear cells are identified by CD3. In some embodiments, PMN-MDSCs are identified by CD40 and an absence of CD14 on the cell surface and peripheral blood mononuclear cells are identified by CD14. In some embodiments, PMN-MDSCs are identified by CD40 and an absence of CD14 on the cell surface and peripheral blood mononuclear cells are identified by CD19. In some embodiments, PMN-MDSCs are identified by CD40 and an absence of CD14 on the cell surface and peripheral blood mononuclear cells are identified by CD56. In some embodiments, PMN-MDSCs are identified by CD40 and an absence of CD14 on the cell surface and peripheral blood mononuclear cells are identified by HLA-DR. In some embodiments, PMN-MDSCs are identified by CD11b and CD33 and an absence of CD14 on the cell surface and peripheral blood mononuclear cells are identified by CD3. In some embodiments, PMN-MDSCs are identified by CD11b and CD33 and an absence of CD14 on the cell surface and peripheral blood mononuclear cells are identified by CD14. In some embodiments, PMN-MDSCs are identified by CD11b and CD33 and an absence of CD14 on the cell surface and peripheral blood mononuclear cells are identified by CD19. In some embodiments, PMN-MDSCs are identified by CD11b and CD33 and an absence of CD14 on the cell surface and peripheral blood mononuclear cells are identified by CD56. In some embodiments, PMN-MDSCs are identified by CD11b and CD33 and an absence of CD14 on the cell surface and peripheral blood mononuclear cells are identified by HLA-DR. In some embodiments, PMN-MDSCs are identified by CD11b and CD33 and an absence of CD14 on the cell surface and peripheral blood mononuclear cells are identified by CD3, CD14, CD19, CD56, and HLA-DR.

In some embodiments, CD14-positive and HLA-DR-(lo/negative) cells, CD14-positive cells, and peripheral blood mononuclear cells are identified by a cell surface marker. Non-limiting examples of cell surface markers that identify peripheral blood mononuclear cells include CD3, CD14, CD19, CD56, and HLA-DR.

In some embodiments, CD14-positive and HLA-DR-(lo/negative) cells are identified by CD14 and a low level or absence of HLA-DR and peripheral blood mononuclear cells are identified by CD3. In some embodiments, CD14-positive and HLA-DR-(lo/negative) cells are identified by CD14 and a low level or absence of HLA-DR and peripheral blood mononuclear cells are identified by CD14. In some embodiments, CD14-positive and HLA-DR-(lo/negative) cells are identified by CD14 and a low level or absence of HLA-DR and peripheral blood mononuclear cells are identified by CD19. In some embodiments, CD14-positive and HLA-DR-(lo/negative) cells are identified by CD14 and a low level or absence of HLA-DR and peripheral blood mononuclear cells are identified by CD56. In some embodiments, CD14-positive and HLA-DR-(lo/negative) cells are identified by CD14 and a low level or absence of HLA-DR and peripheral blood mononuclear cells are identified by HLA-DR. In some embodiments, CD14-positive and HLA-DR-(lo/negative) cells are identified by CD14 and a low level or absence of HLA-DR and peripheral blood mononuclear cells are identified by CD3, CD14, CD19, CD56, and HLA-DR. In some embodiments, CD14-positive and HLA-DR-(lo/negative) cells are identified by CD14 and a low level or absence of HLA-DR and CD14-positive cells are identified by CD14.

Additional Therapy

Available additional treatments for triple negative breast cancer that may be advantageously employed in combination with the therapies disclosed herein include, without limitation, radiation therapy, chemotherapy, antibody therapy, and tyrosine kinase inhibitors as adjuvant therapy.

Radiation therapy is a cancer treatment that uses high-energy x-rays or other types of radiation to kill cancer cells or keep them from growing. Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Different chemotherapeutic agents are known in the art for treating lung cancer. Cytoxic agents used for treating lung cancer include carboplatin (for example, Paraplatin®, Paraplat®), cisplatin (for example, Platinol®, Platinol-Aq®), crizotinib (for example Xalkori®), etoposide (for example Toposar®, VePesid®), etoposide Phosphate (for example Etopophos®), gemcitabine hydrochloride (for example Gemzar®), gemcitabine-cisplatin, methotrexate (for example Abitrexate®, Folex®, Folex Pfs®, Methotrexate Lpf®, Mexate®, Mexate-Aq®), paclitaxel (for example Taxol®), pemetrexed Disodium (for example Alimta®), and topotecan Hydrochloride (for example Hycamtin®)

Different agents are known in the art for treating melanoma, including aldesleukin (for example Proleukin®), dabrafenib (for example Tafinlar®), dacarbazine (for example DTIC-Dome®), recombinant Interferon Alfa-2b (for example Intron® A), Ipilimumab (for example Yervoy®), pembrolizumab (for example Keytruda®), Trametinib (for example Mekinist®), Nivolumab (for example Opdivo®), Peginterferon Alfa-2b (for example Pegintron®, Sylatron®), vemurafenib (for example Zelboraf®).

Monoclonal antibody therapy is a cancer treatment that uses antibodies made in the laboratory, from a single type of immune system cell. These antibodies can identify substances on cancer cells or normal substances that may help cancer cells grow. The antibodies attach to the substances and kill the cancer cells, block their growth, or keep them from spreading. Monoclonal antibodies are given by infusion. They may be used alone or to carry drugs, toxins, or radioactive material directly to cancer cells. Monoclonal antibodies are also used in combination with chemotherapy as adjuvant therapy.

Additional, illustrative, treatments that may be advantageously combined with the compositions and therapies disclosed herein may include, without limitation, administration of agents including, but not limited to lapatinib, alone or in combination with capecitabine, docetaxel, epirubicin, epothilone A, B or D, goserelin acetate, paclitaxel, pamidronate, bevacizumab, or trastuzumab.

In some embodiments, the additional therapy comprises chemotherapy comprising administering to the subject one or more of doxorubicin, cyclophosphamide, paclitaxel, lapatinib, capecitabine, trastuzumab, bevacizumab, gemcitabine, eribulin, or nab-paclitaxel.

Oral Formulations

Oral formulations containing the active pharmaceutical ingredients described herein may comprise any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Oral Administration

As described herein, the combination therapy described herein can be given simultaneously or can be given in a staggered regimen, with entinostat being given at a different time during the course of chemotherapy than the EGFR inhibitor. This time differential may range from several minutes, hours, days, weeks, or longer between administrations of the two compounds. Therefore, the term combination does not necessarily mean administered at the same time or as a unitary dose, but that each of the components are administered during a desired treatment period. The agents may also be administered by different routes. As is typical for chemotherapeutic regimens, a course of chemotherapy may be repeated several weeks later, and may follow the same timeframe for administration of the two compounds, or may be modified based on patient response.

In other embodiments, the pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glyceryl behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carboxymethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In other embodiments, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

In further embodiments, the pharmaceutical compositions provided herein may be co-formulated with other active ingredients which do not impair the desired therapeutic action, or with substances that supplement the desired action.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The disclosure having now been described by way of written description, those of skill in the art will recognize that the disclosure can be practiced in a variety of embodiments and that the foregoing description and examples below are for purposes of illustration and not limitation of the claims that follow.

EXAMPLES

Example 1. Modulation of Myeloid Derived Suppressor Cells by Entinostat

Blood samples were obtained from a set of 49 patients enrolled in the ENCORE 301 clinical trial, all of whom had advanced hormone receptor-positive breast cancer and had progressed on a non-steroidal aromatase inhibitor. 27 patients received exemestane and entinostat ("EE") and 22 received exemestane and placebo ("EP"). Blood samples were obtained on cycle 1 day 1 (C1D1; pre-treatment), C1D2, C1D8, and C1D15 for biomarker analyses. Of these patient samples, 34 (20 EE and 14 EP) were analyzed for circulating immune subsets. Cell populations were based on the following surface markers, in which "X−" means negative for marker X, "X+" means positive for marker X, "Xlow/−" means low levels to absence of marker X, and "Xhi" means high levels of expression of marker X:

Myeloid derived suppressor cell: CD3−, CD19−, CD56−, HLA-DR−, CD11b+, CD33+.

PMN-MDSC: CD14−, CD11b+, CD33+.

M-MDSC: CD3−, CD19−, CD56−, HLA-DR−, CD11b+, CD33+, CD14+.

Immature MDSC: CD3−, CD19−, CD56−, HLA-DR−, CD11b+, CD33+, CD14−.

CD8+ T-cell: CD4−, CD8+, Foxp3−.

CD4+ T-cell: CD8−, CD4+, Foxp3−.

$T_{regs}$: CD4+, CD8−, CD25hi, Foxp3+.

Monocytes were analyzed for three populations: (1) CD14+; (2) CD14+, HLA-DRhi; and (3) CD14+, HLA-DRlow/−. PD-1, CTLA-4, and TIM-3 were measured on CD8+ T-cells, CD4+ T-cells, and $T_{regs}$, and CD40 was measured on myeloid derived suppressor cells.

All comparisons were performed between the C1D1 and the C1D15 time points in the EE and EP treatment groups. For PMN-MDSCs, EE treatment led to a change of −14.67%, while EP treatment led to a change of +20.56%. For M-MDSCs, EE treatment led to a change of −62.3%, while EP treatment led to a change of +1.97%. For immature MDSCs, EE treatment led to a change of −20.9%, while EP treatment led to a change of −15.0%. In myeloid derived suppressor cells, M-MDSCs, PMN-MDSCs, and immature myeloid derived suppressor cells, CD40 levels were reduced in the EE treatment group compared to the EP treatment group. For HLA-DR+ monocytes, EE treatment led to a change of +34.1%, while EP treatment led to a change of −11.38%. On monocytes, HLA-DR levels were +16.3% in the EE treatment group and −4.7% in the EP treatment group.

Example 2. Modulation of CD14$^+$-HLA-DR(Lo/Negative) Myeloid Derived Suppressor Cells by Entinostat Combination Therapy Entinostat, a class I HDAC inhibitor (HDACi), has shown promising activity in ENCORE 301, a randomized, placebo-controlled, phase II trial of entinostat plus exemestane ("EE") vs. exemestane plus placebo ("EP") in advanced hormone receptor positive breast cancer that had progressed on non-steroidal aromatase inhibitors. ENCORE 301 met the primary progression free survival end-point and showed a median 8.3 month improvement in the overall survival (OS) endpoint for the EE arm. Based on those results entinostat was granted breakthrough therapy designation and a Phase 3 trial, E2112 comparing EE to EP is currently enrolling. Emerging preclinical work suggests that entinostat has immunomodulatory effects on immune suppressor cells including regulatory T cells (Tregs) and myeloid derived suppressor cells (MDSCs) and can eradicate modestly immunogenic mouse tumors in combination with immune checkpoint blockade agents. This activity was shown to be mediated via reduction of MSDCs (Kim et al., PNAS 2014, 111:11774-9). These results may be explained by entinostat's selective targeting of those class 1 HDAC enzymes which have been shown to play a role in the differentiation and activation of Tregs (Shen et al. PLoS One 2012, 7:e30815; Wang et al. JCI 2015, 125:1111-1123) and MDSCs (Youn et al. Nat. Immunol 2013, 14:211-220).

Based on these data, an analysis was conducted of immune subsets in blood samples from ENCORE 301 breast cancer patients.

Blood was collected from a subset of 49 patients (27 EE and 22 EP) representative of the 130 patients enrolled in ENCORE 301 on cycle 1 day 1 (C1D1; pretreatment), C1D2, C1D8, and C1D15 for biomarker analyses. Of these 49, C1D1 and C1D15 samples were available from 34 patients (20 EE and 14 EP) for further analysis of circulating immune subsets. The clinical outcome for Progression Free Survival (PFS) was found to be 4.9 months for EE (Entinostat+Exemestane) patients, 1.8 months for (Exemestane and +Placebo) with a hazard ratio (HR) of 0.62 months and Overall Survival (OS) was found to be 28.1 months for EE, 20.3 months for EP, with a HR of 0.62 months, in the 34 patients as well as baselined demographics was consistent with the intent-to-treat population.

The percent change in subsets at C1D15 vs. baseline was assessed based on the following surface markers: Lin-MDSC (lin;CD3,CD19,CD56)-HLA-DR-CD11b+CD33+), granulocytic MDSC (CD14-CD11b+CD33+), monocytic MDSC (Lin-HLA-DR-CD11b+CD33+CD14+), immature MDSC (Lin-HLA-DR-CD11b+CD33+CD14-), CD8+T-cells (CD4-CD8+), Foxp3-CD4+T-cells (CD8-CD4+Foxp3-), and Tregs (CD4+CD8-CD25hiFoxp3+). Monocytes were analyzed for three populations: CD14+, CD14+HLA-DRhi, and CD14+HLA-DR-low/negative. In addition, PD-1, CTLA-4, and TIM-3 were measured on T-cell subsets, and CD40 was measured on MDSCs.

In line with preclinical data, a reduction in granulocytic MDSC (−14.67% vs. +20.56%, P=0.03) and monocytic MDSC (−62.3% vs. +1.97%, P=0.002) was observed in EE. Interestingly, CD40, a costimulatory receptor required for MDSC-mediated immune suppression was also down-regulated in all MDSC subsets. Entinostat did not significantly impact the ratio of CD8+ T-cells to CD4+ T-cells or alter expression of CTLA-4, PD-1, or TIM-3 on T-cell subsets. Reduced expression of HLA-DR on monocytes has been associated with poor prognosis in cancer. Consistent with entinostat-mediated immunomodulatory effects, an increase in the number of HLA-DR+ monocytes (34.1% vs. −11.38%, P=0.0004) and level of HLA-DR expression on monocytes (16.3% vs. −4.7%; P=0.015) was observed. No correlation was identified between the C1D15 immune cell changes and clinical outcome in this subset of patients.

Results are shown in Table 1 below.

TABLE 1

Effect of EE vs EP treatment on surface markers

| Lab Test Name | EP (n = 14; change from baseline to C1D15 (%)) | | EE (n = 20; change from baseline to C1D15 (%)) | | p-value (EE vs EP) |
|---|---|---|---|---|---|
| | Mean (SD) | Median (Min, Max) | Mean (SD) | Median (Min, Max) | |
| CD14+ | −0.58 (22.73) | 1.90 (−38.67, 42.09) | 15.71 (28.49) | 13.12 (−22.76, 65.47) | 0.16 |
| CD14+HLA-DR$^{HI}$ | −8.63 (17.77) | −11.38 (−37.35, 25.37) | 41.76 (44.28) | 34.08 (−25.35, 123.84) | 0.0004 |
| CD14+HLA-DR$^{LO/NEG}$ | 13.45 (43.11) | 1.55 (−41.10, 93.38) | 3.56 (42.07) | −3.46 (−47.33, 66.14) | 0.45 |
| HLA-DR expression on CD14+ | −6.23 (18.77) | −4.74 (−32.46, 29.94) | 23.20 (36.69) | 16.26 (−36.75, 89.30) | 0.02 |
| g-MDSCs | 20.56 (68.45) | 3.82 (−72.47, 224.31) | −14.67 (65.78) | −34.53 (−77.75, 220.55) | 0.03 |
| CD40 on g-MDSCs | 16.52 (32.07) | 10.52 (−27.59, 75.76) | −0.35 (30.88) | −0.72 (−47.74, 50.00) | 0.22 |
| m-MDSCs | 28.24 (86.60) | 1.97 (−55.05, 241.46) | −44.94 (50.22) | −62.33 (−92.81, 85.71) | 0.002 |
| CD40 on m-MDSCs | 3.37 (25.69) | 1.57 (−45.55, 73.91) | −16.75 (21.37) | −17.18 (−61.05, 25.29) | 0.011 |
| Lin-MDSCs | 1.28 (83.31) | −22.11 (−58.15, 274.45) | −13.26 (58.66) | −29.03 (−83.61, 120.51) | 0.611 |
| CD40 on Lin-MDSCs | 14.85 (34.92) | 3.37 (−26.61, 97.78) | −16.67 (26.47) | −15.38 (−71.05, 21.82) | 0.02 |
| immature MDSCs | 4.92 (94.50) | −20.94 (−68.27, 306.60) | 18.75 (130.14) | −14.95 (−89.23, 467.57) | 0.93 |
| CD40 on immature MDSCs | 18.64 (35.15) | 9.00 (−32.58, 86.36) | −11.61 (21.90) | −8.51 (−49.30, 31.25) | 0.007 |

Figure 1:
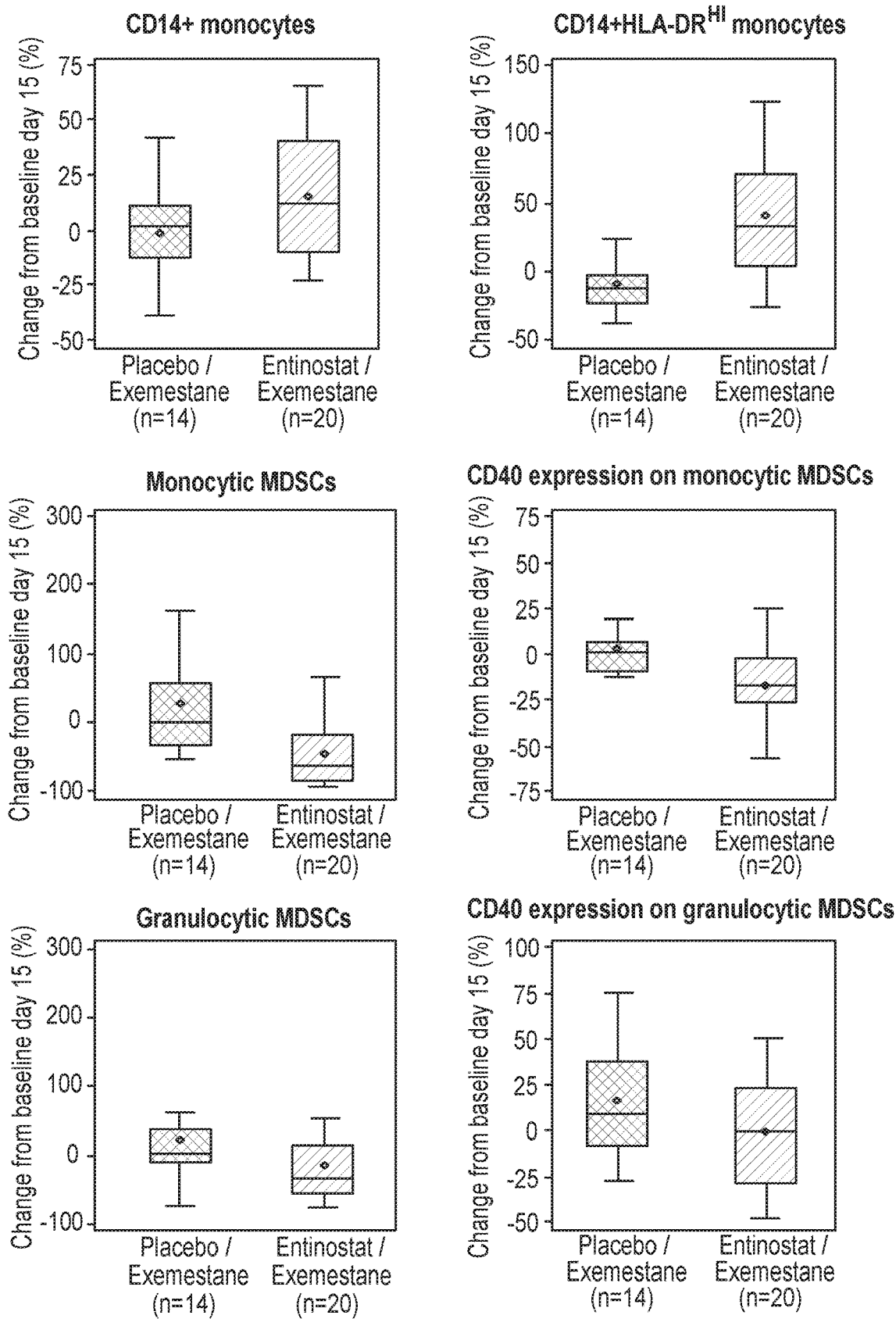
FIG. 1 illustrates percentage change of CD14+ cell number, CD14+HLA-DR$^{Hi}$ monocyte cell number, monocytic MDSCs cell number, CD40 expression on monocytic MDSCs, granulocytic MDSCs cell number, and CD40 expression on monocytic MDSCs, in blood samples obtained from selected patients from ENCORE 301 trial, between baseline to day 15 of treatment with either a combination of entinostat and exemestane (EE) or a combination of exemestane and placebo.
Figure 2B:
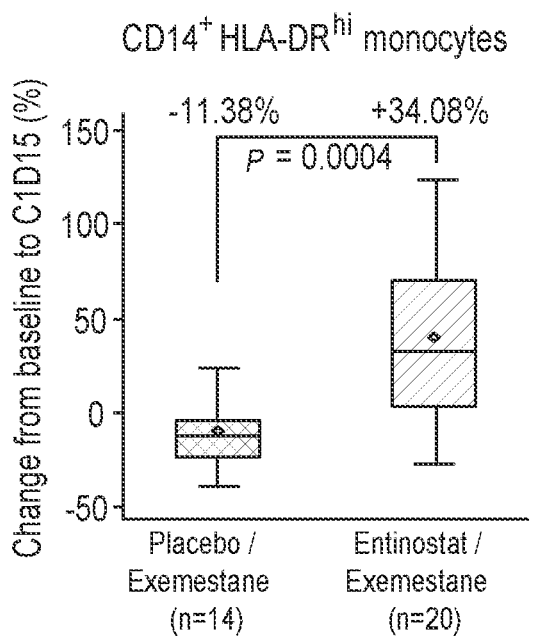
Figure 2C:
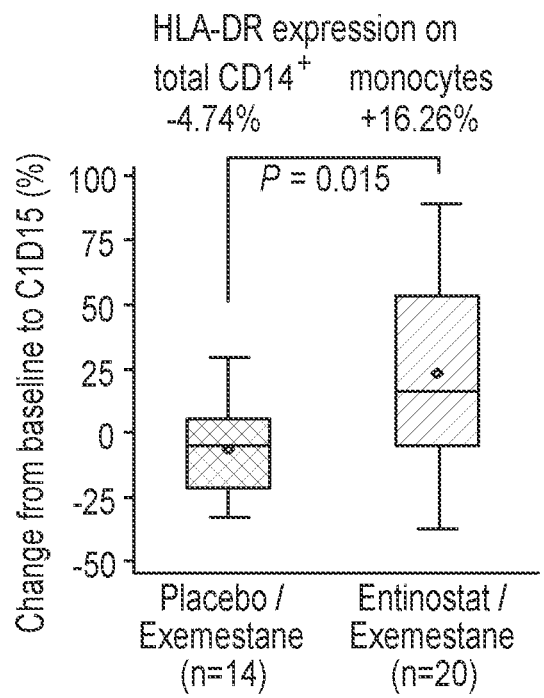
Figure 2D:
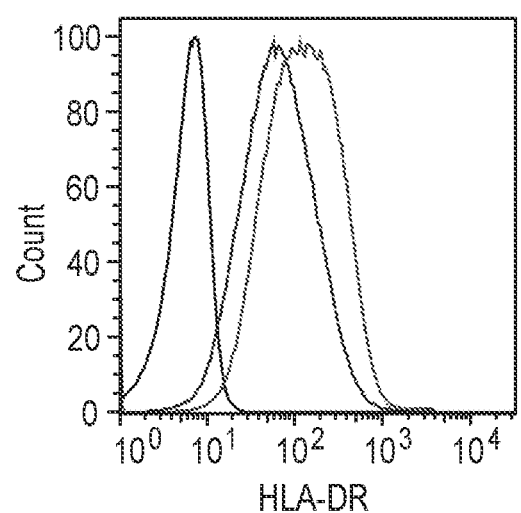
Figure 2D:
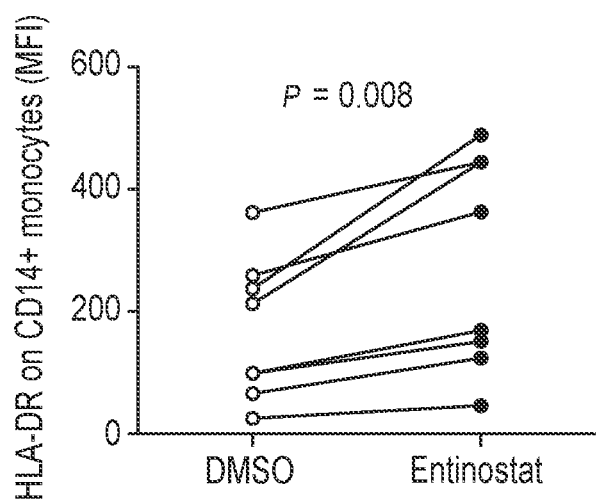

Further, as seen in FIG. 1, for HLA-DR+ monocytes, EE treatment led to a change of +34.1%, while EP treatment led to a change of −11.38%. On monocytes, HLA-DR levels were +16.3% in the EE treatment group and −4.7% in the EP treatment group. More data are shown in FIGS. 2-5. The methods and results are also described in Tomita et al., "The interplay of epigenetic therapy and immunity in locally recurrent or metastatic estrogen receptor-positive breast cancer: Correlative analysis of ENCORE 301, a randomized, placebo-controlled phase II trial of exemestane with or without entinostat", ONCOINIMUNOLOGY, Taylor and Francis Online, 2016, the entire contents of which are hereby incorporated by reference in its entireties.

In summary, data from blood samples obtained from ER+ breast cancer patients treated with entinostat combined with exemestane in ENCORE 301 provided the first evidence of HDACi-mediated reduction of immunosuppressive MDSCs and increased immunocompetent CD14+HLA-DR$^{HI}$ monocytes in patients. These findings may in part explain the improved OS seen with EE in ENCORE 301 and provide strong rationale for planned combination studies of entinostat with immune checkpoint blockade.

The reduction in MDSCs in entinostat treated patients was consistent with recently published preclinical work (Kim et al PNAS 2014) demonstrating entinostat's ability to enhance the anti-tumor activity of immune checkpoint inhibitors through reduction of MDSCs. A phase 1b/2 trial of entinostat in combination with pembrolizumab in NSCLC and melanoma has been initiated to determine the safety and clinical benefit of the combination.

A phase 1b/2 trial of entinostat in combination with atezolizumab in TNBC is planned.

Additional preclinical and clinical studies are ongoing to further explore entinostat's immunomodulatory activity.

Example 3. Patient Selection for Entinostat Combination Therapy with Exemestane

To select a patient for treatment with entinostat in combination with exemestane, a peripheral blood sample is taken from the patient. The patient is a post-menopausal woman diagnosed with metastatic hormone-receptor positive breast cancer who has progressed during treatment with a non-steroidal aromatase inhibitor. The 5 milliliter (mL) peripheral blood sample is taken into EDTA collection tubes, which are rapidly cooled on ice. Blood samples are transferred to a conical tube and diluted with 15 mL of red blood cell lysis buffer and incubated at room temperature for 10 minutes. Red blood cell lysis is quenched by dilution with 30 mL phosphate-buffered saline (PBS). The cell suspension is centrifuged 5 minutes at 400×g at 4° C. and the supernatant is discarded. The pellet is resuspended in 5 mL of PBS and transferred to a new conical tube. The resuspended sample is underlaid with 5 mL Ficoll®. Cells are centrifuged for 20 minutes 400×g with the brake turned off on the centrifuge. Nucleated cells are harvested at the interface of the PBS and Ficoll® layers into a fresh conical tube.

An equal volume to the original blood draw is added to the pellet in the fresh conical tube to wash the cells. The cell suspension is centrifuged 5 minutes at 400×g at 4° C. and the supernatant is discarded. Cells are resuspended in an equal volume to the original blood draw in PBS with 1% bovine serum albumin and 0.5% EDTA (staining buffer). Viable cells are then counted using a hemacytometer. The cell suspension is centrifuged 5 minutes at 400×g at 4° C., the supernatant is discarded, and the cells are resuspended in Staining Buffer to a cell concentration of about $10^7$ cells per mL and 1 mL aliquots are transferred to new tubes.

In a first study, the following antibodies are added to the resuspended cells: FITC-conjugated anti-CD11b; PE-conjugated anti-CD33; PerCP-Cy™5.5-conjugated anti-CD14; and APC-conjugated anti-CD3, anti-CD19, anti-CD56, and anti-HLA-DR. In a second study, the following antibodies are added to the resuspended cells: FITC-conjugated anti-CD14; PE-conjugated anti-HLA-DR; and APC-conjugated anti-CD3, anti-CD19, and anti-CD56. In a third study, the following antibodies are added to the resuspended cells: FITC-conjugated anti-CD14 and PE-conjugated anti-HLA-DR. Control samples include unstained cells and stained cells in which one of each of the set of fluorochrome antibodies is left out. Cells are covered to minimize light exposure and left at room temperature for 20 minutes.

Stained cells are washed twice in staining buffer by centrifugation for 5 minutes at 400×g at 4° C., discarding of the supernatant, and resuspension in an equal volume of staining buffer. Stained cells are then transferred to polypropylene tubes for use on the flow cytometer.

Flow cytometry is performed on a Cytomics FC 500 flow cytometer, which automates tube-based acquisition of flow cytometry data. After performance of the automated run, samples are corrected both for background fluorescence (using the unstained sample) and fluorochrome compensation (using the individually left out fluorochrome samples). In the first study, antibody-cell complexes are then calculated for myeloid derived suppressor cells, identified by CD11b and CD33 positivity and CD3, CD19, CD56, HLA-DR negativity, and Peripheral blood mononuclear cells, identified by CD3, CD14, CD19, CD56, and HLA-DR positivity and CD11b and CD33 negativity. These values for the antibody-cell complexes are used to calculate the ratio of myeloid derived suppressor cells to peripheral blood mononuclear cells. In this setting, if the patient has a ratio of between 1:100 and 1:1, indicating the presence of elevated numbers of myeloid derived suppressor cells, the patient is selected for combination therapy with entinostat and exemestane. In the second study, CD14-positive and HLA-DR-lo/negative cells are identified by CD14 positivity, HLA-DR low expression or negativity, and CD3, CD19, and CD56 negativity. Peripheral blood mononuclear cells, identified by CD3, CD19, CD56, and HLA-DR positivity. These values are used to calculate the ratio of CD14-positive and HLA-DR-lo/negative cells to peripheral blood mononuclear cells. In this setting, if the patient has a ratio of between 1:200 and 1:1, indicating the presence of elevated numbers of CD14-positive and HLA-DR-lo/negative cells, the patient is selected for combination therapy with entinostat and exemestane. In the third study, CD14-positive and HLA-DR-lo/negative cells are identified by CD14 positivity and HLA-DR low expression or negativity. CD14-positive cells are identified by CD14 positivity independent of HLA-DR expression. These values are used to calculate the ratio of CD14-positive and HLA-DR-lo/negative cells to CD14-positive cells. In this setting, if the patient has a ratio of between 1:100 and 99:1, indicating the presence of elevated numbers of CD14-positive and HLA-DR-lo/negative cells, the patient is selected for combination therapy with entinostat and exemestane.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of selecting a patient for combination therapy comprising entinostat and a second therapeutic agent comprising:
   obtaining a peripheral blood sample from the patient, wherein the patient is diagnosed with a melanoma or lung cancer;
   measuring the number of myeloid derived suppressor cells and peripheral blood mononuclear cells in the peripheral blood sample; and
   administering the combination therapy to the patient if the ratio of myeloid derived suppressor cells to peripheral blood mononuclear cells is between 1:200 and 1:4.

2. The method of claim 1, wherein the peripheral blood sample is treated with an anticoagulant.

3. The method of claim 2, wherein the anticoagulant is EDTA or heparin.

4. The method of claim 1, wherein measuring the myeloid derived suppressor cell population and the PBMC population is performed by flow cytometry or by cytospin.

5. The method of claim 1, wherein the myeloid derived suppressor cell population or the peripheral blood mononuclear cell population is identified by a cell surface marker.

6. The method of claim 5, wherein the cell surface marker is at least one of CD11b, CD33, and CD40 or at least one of CD3, CD14, CD19, CD56, and HLA-DR.

7. The method of claim 1, wherein the myeloid derived suppressor cell is a polymorphonuclear-MDSC.

8. The method of claim 7, wherein the polymorphonuclear-MDSC is identified by a cell surface marker.

9. The method of claim 8, wherein the cell surface marker is CD15.

10. The method of claim 1, wherein the myeloid derived suppressor cell is a monocytic-MDSC.

11. The method of claim 10, wherein the monocytic-MDSC is identified by a cell surface marker.

12. The method of claim 11, wherein the cell surface marker is CD14.

13. The method of claim 1, wherein the ratio is between 1:100 and 1:4, between 1:50 and 1:4, between 1:20 and 1:4, between 1:10 and 1:4 or between 1:5 and 1:4.

14. The method of claim 1, wherein the entinostat is administered first, is administered weekly, or is administered every two weeks.

15. The method of claim 1, wherein the second therapeutic agent is an anti-PD-1 antibody, an anti-PD-L1 antibody, or is exemestane.

16. The method of claim 15, wherein the anti-PD-1 antibody is pembrolizumab or nivolumab.

17. The method of claim 1, wherein the melanoma cancer is a metastatic melanoma.

18. The method of claim 1, wherein the lung cancer is a non-small cell lung cancer, squamous cell carcinoma, or large cell carcinoma.

19. The method of claim 15, wherein the anti-PD-1 antibody is pembrolizumab.

* * * * *